United States Patent [19]

Spooner et al.

[11] Patent Number: 5,885,808
[45] Date of Patent: Mar. 23, 1999

[54] ADENOVIRUS WITH MODIFIED BINDING MOIETY SPECIFIC FOR THE TARGET CELLS

[75] Inventors: Robert Anthony Spooner; Agamemnon Antoniou Epenetos, both of London, United Kingdom

[73] Assignee: Imperial Cancer Research Technology Limited, London, United Kingdom

[21] Appl. No.: 428,257

[22] PCT Filed: Nov. 4, 1993

[86] PCT No.: PCT/GB93/02267

§ 371 Date: Jul. 5, 1995

§ 102(e) Date: Jul. 5, 1995

[87] PCT Pub. No.: WO94/10323

PCT Pub. Date: May 11, 1994

[30] Foreign Application Priority Data

Nov. 4, 1992 [GB] United Kingdom .................. 9223084

[51] Int. Cl.[6] ........................... C12N 15/86; C12N 15/34; A61K 39/235
[52] U.S. Cl. ................. 435/172.3; 424/93.2; 435/320.1; 536/23.1; 536/23.4; 536/23.72
[58] Field of Search ............................... 435/320.1, 172.3; 424/93.1, 93.2; 536/23.1, 23.4, 23.72

[56] References Cited

U.S. PATENT DOCUMENTS

| 5,543,328 | 8/1996 | McClelland et al. ................. 435/320.1 |
| 5,559,099 | 9/1996 | Wickham et al. ........................ 514/44 |

FOREIGN PATENT DOCUMENTS

| 535576 | 9/1992 | European Pat. Off. . |
| WO8803563 | 5/1988 | WIPO . |
| WO 90/07936 | 7/1990 | WIPO . |
| WO 90/12087 | 10/1990 | WIPO . |
| WO9203545 | 3/1992 | WIPO . |
| WO9222641 | 12/1992 | WIPO . |

OTHER PUBLICATIONS

"Report and Recommendations of the Panel to Access the NIH Investment in Research on Gene Therapy," Orkin and Motulsky, Co–chairs, Dec. 7, 1995.
Wagner et al., Proc. Natl. Acad. Sci. USA 89:6099–6103 (1992).
Falgout et al., Journal of Virology 62(2):622–625 (1988).
Wickham et al., Cell 73:309–319 (1993).
Coghlan, New Scientist 148:14–15 (1995).
Seth et al, "Evidence that the Penton Base of Adenovirus is Involved in Potentiation of Toxicity of Pseudomonas Exotoxin Conjugated to Epidermal Growth Factor", *Mol. and Cell. Biology*, No. 8. Aug. 1984, pp. 1528–1533.
Mittal et al "Monitoring foreign gene expression by a human adenovirus–based vector using the firefly luciferase gene as a reporter", Virus Research, 28 (1993) 67–90.
Immunology Today, vol. 11, No. 6, 1990, p. 198.
T. Friedman, "Progress Toward Human Gene Therapy", Science, vol. 244, Jun. 16, 1989, pp. 1275–1281.
Adams et al, "The expression of hybrid HIV:Ty virus–like particles in yeast", Nature, vol. 329, Sep. 3, 1987, pp. 68–70.
Ezzeddine, et al, "Selective Killing of Glioma Cells in Cuture and in Vivo by Retrovirus Transfer of the Herpes Simplex Virus Thymidine Kinase Gene", The New Biologist, vol. 3, No. 6 (Jun.) 1991; pp. 608–614.

*Primary Examiner*—Johnny F. Railey, II
*Attorney, Agent, or Firm*—McAulay Nissen Goldberg Kiel & Hand, LLP

[57] ABSTRACT

An adenovirus or adenovirus-like particle which has a modified binding specificity conferred by a binding moiety. The binding moiety is heterologous to the adenovirus and is incorporated as a fusion protein with the fiber protein. This allows the adenovirus or adenovirus-like particle to bind to a target cell which is not the natural host cell of the virus. The penton fiber is modified by the insertion or, deletion, or substitution of amino acid residues, that disrupt the host-cell binding function so that the adenovirus or adenovirous like particle does not bind the natural host cell.

14 Claims, 23 Drawing Sheets

Fusion A

```
                  1  2  3  4              108 109
       P   L   V   T   S   N   V   Q   L  ..........L   E   *   *
       CCTCTAGTTACCTCCAATGTGCAGCTGCAG...ScFv...CTCGAGTAATAAGAATTC
         31210           |       PstI  ..    .XhoI        EcoRI
```

Fusion B

```
                  1  2  3  4              108 109
       L   S   L   D   E   A   V   Q   L  ..........L   E   *   *
       CTCTCTCTGGACGAGGCCGTGCAGCTGCAG...ScFv...CTCGAGTAATAAGAATTC
         31260           |       PstI  ..    .XhoI        EcoRI
```

Fusion C

```
                  1  2  3  4              108 109
       P   L   K   K   T   K   V   Q   L  ..........L   E   *   *
       CCTCTCAAAAAAACCAAGGTGCAGCTGCAG...ScFv...CTCGAGTAATAAGAATTC
         31310    31320  |       PstI  ..    .XhoI        EcoRI
```

Fusion D

```
                  1  2  3  4              108 109
       P   L   T   V   T   S   V   Q   L  ..........L   E   *   *
       CCCCTCACAGTTACCTCAGTGCAGCTGCAG...ScFv...CTCGAGTAATAAGAATTC
         31360           |       PstI  ..    .XhoI        EcoRI
```

Fusion E

```
                  1  2  3  4              108 109
       P   L   M   V   A   D   V   Q   L  ..........L   E   *   *
       CCTCTAATGGTCGCGGGCGTGCAGCTGCAG...ScFv...CTCGAGTAATAAGAATTC
         31400    31410  |       PstI  ..    .XhoI        EcoRI
```

FIGURE 6A

```
Fusion F
                       1  2  3  4          108 109
       P   L   T   V   H  D  V  Q  L ..........L  E  *  *
       CCGCTAACCGTGCACGACGTGCAGCTGCAG...ScFv...CTCGAGTAATAAGAATTC
          31450           |      PstI ..        .XhoI      EcoRI Fusion G
                       1  2  3  4          108 109
       P   L   T   V   S  E  V  Q  L ..........L  E  *  *
       CCCCTCACAGTGTCAGAAGTGCAGCTGCAG...ScFv...CTCGAGTAATAAGAATTC
          31490      31500 |    PstI ..        .XhoI      EcoRI Fusion H
                       1  2  3  4          108 109
       L   T   T   T   D  S  V  Q  L ..........L  E  *  *
       CTCACCACCACCGATAGCGTGCAGCTGCAG...ScFv...CTCGAGTAATAAGAATTC
          31540      31550 |    PstI ..        .XhoI      EcoRI Fusion I
                       1  2  3  4          108 109
       P   L   T   T   A  T  V  Q  L ..........L  E  *  *
       CCTCTAACTACTGCCACTGTGCAGCTGCAG...ScFv...CTCGAGTAATAAGAATTC
          31590           |      PstI ..        .XhoI      EcoRI Fusion J
                       1  2  3  4          108 109
       P   I   Y   T   Q  N  V  Q  L ..........L  E  *  *
       CCCATTTATACACAAAATGTGCAGCTGCAG...ScFv...CTCGAGTAATAAGAATTC
          31630      31640 |    PstI ..        .XhoI      EcoRI
```

FIGURE 6B

Fusion K

```
                    1   2   3   4            108  109
         H   V   T   D   D   L   V   Q   L   Q..........L   E   *   *
         CATGTAACAGACGACCTAGTGCAGCTGCAG...ScFv...CTCGAGTAATAAGAATTC
            31730         |      PstI  ..    .XhoI       EcoRI
```

Fusion L

```
                    1   2   3   4            108  109
         G   V   T   I   N   N   V   Q   L   Q..........L   E   *   *
         GGTGTGACTATTAATAATGTGCAGCTGCAG...ScFv...CTCGAGTAATAAGAATTC
            31730         |      PstI  ..    .XhoI       EcoRI
```

Fusion M

```
                    1   2   3   4            108  109
         G   F   D   S   Q   G   V   Q   L   Q..........L   E   *   *
         GGTTTTGATTCACAAGGCGTGCAGCTGCAG...ScFv...CTCGAGTAATAAGAATTC
            31780         |      PstI  ..    .XhoI       EcoRI
```

Fusion N

```
                    1   2   3   4            108  109
         R   I   D   S   Q   N   V   Q   L   Q..........L   E   *   *
         AGGATTGATTCTCAAAACGTGCAGCTGCAG...ScFv...CTCGAGTAATAAGAATTC
            31830         |      PstI  ..    .XhoI       EcoRI
```

Fusion O

```
                    1   2   3   4            108  109
         F   D   A   Q   N   Q   V   Q   L   Q..........L   E   *   *
         TTTGATGCTCAAAACCAAGTGCAGCTGCAG...ScFv...CTCGAGTAATAAGAATTC
            31880         |      PstI  ..    .XhoI       EcoRI
```

FIGURE 6C

```
Fusion P
                          1  2  3  4           108 109
          P  F  I  N  S  A  V  Q  L  Q..........L   E   *  *
          CTTTTTATAAACTCAGCCGTGCAGCTGCAG...ScFv...CTCGAGTAATAAGAATTC
             31920            |   PstI  ..     .XhoI         EcoRI Fusion Q
                          1  2  3  4           108 109
          S  N  N  S  K  N  V  Q  L  Q..........L   E   *  *
          TCAAACAATTCCAAAAACGTGCAGCTGCAG...ScFv...CTCGAGTAATAAGAATTC
             32030     32040|      PstI  ..     .XhoI         EcoRI Fusion R
                          1  2  3  4           108 109
          G  L  M  F  D  A  V  Q  L  Q..........L   E   *  *
          GGGTTGATGTTTGACGCTGTGCAGCTGCAG...ScFv...CTCGAGTAATAAGAATTC
             32030     32040|      PstI  ..     .XhoI         EcoRI Fusion S
                          1  2  3  4           108 109
          P  N  A  P  N  T  V  Q  L  Q..........L   E   *  *
          CCTAATGCACCAAACACAGTGCAGCTGCAG...ScFv...CTCGAGTAATAAGAATTC
             32100    |           PstI  ..     .XhoI         EcoRI Fusion T
                          1  2  3  4           108 109
          L  E  F  D  S  N  V  Q  L  Q..........L   E   *  *
          CTAGAATTTGATTCAAACGTGCAGCTGCAG...ScFv...CTCGAGTAATAAGAATTC
             32150  |             PstI  ..     .XhoI         EcoRI
```

FIGURE 6D

Fusion U

```
                    1  2  3  4           108 109
        L  S  F  D  S  T  V  Q  L  Q ..........L  E  *  *
        CTTAGTTTTGACAGCACAGTGCAGCTGCAG...ScFv...CTCGAGTAATAAGAATTC
          32190            |    PstI ..          .XhoI       EcoRI
```

Fusion V

```
                    1  2  3  4           108 109
        I  D  K  L  T  L  V  Q  L  Q ..........L  E  *  *
        ATTGATAAGCTAACTTTGGTGCAGCTGCAG...ScFv...CTCGAGTAATAAGAATTC
          32240            |    PstI ..          .XhoI       EcoRI
```

FIGURE 6E

LEADHBACK    AGCTAAGCTTGCATGCAAATTC
                 HindIII SphI

LEADbFOR     pelB leader|
              P   A   M   A   R   S   Q   L   Q
             CCAGCGATGGCCAGATCTCAGCTGCAGAGCT
                           BglII      PstI

FIGURE 7

```
              10         20        30         40         50
                                               M   K   Y   L   L   P
AAGCTTGCATGCAAATTCTATTTCAAGGAGACAGTCATAATGAAATACCTATTGCCT
HindIIISphI             SD                    /------------------

60        70        80         90        100        110
 T   A   A   A   G   L   L   L   L   A   A   Q   P   A   M   A   R   S   Q
ACGGCAGCCGCTGGATTGTTATTACTCGCTGCCCAACCAGCGATGGCCAGATCTCAG
------pelB leader ----------------------------| BglII|V_H 120        130
 L   Q   V   D   G   S
CTGCAGGTCGACGGATCC
PstI    SalI   EcoRI
```

FIGURE 9

```
                         R  S  M  K  R  A  R  P
TAILbBACK         AGCTAGATCTATGAAGCGCGCAAGACCG
                      BglII

FIBRE3FOR         --fibre----------/--scFv-------
                   P  L  N  R  A  R  Q  V  Q  L  Q
                  CCTCTCAAAAAAACCAAGCAGGTGCAGCTGCAGCAGCCTGG
                                                PstI FIBRE6FOR         --fibre----------/--scFv-------
                   P  L  T  V  H  D  Q  V  Q  L  Q
                  CCCGCTAACCGTGCACGACCAGGTGCAGCTGCAGCAGCCTGG
                                                PstI FIBRE9FOR         --fibre----------/--scFv-------
                   P  L  T  T  A  T  Q  V  Q  L  Q
                  CCTCTAACTACTGCCACTCAGGTGCAGCTGCAGCAGCCTGG
                                                PstI FIBRE12FOR        --fibre----------/--scFv-------
                   G  V  T  I  N  N  Q  V  Q  L  Q
                  GGTGTGACTATTAATAATCAGGTGCAGCTGCAGGACCCTGG
                                                PstI FIBRE15FOR        --fibre-------------/--scFv-------
                   P  F  D  A  Q  N  Q  V  Q  L  Q
                  CCGTTTGATGCTCAAAACCAACAGGTGCAGCTGCAGCAGCC
                                                PstI
```

FIGURE 12A

```
FIBRE18FOR        --fibre----------/--scFv-------
                   G   L   M   F   D   G   Q   V   Q   L   Q
                  GGGTTGATGTTTGACGCTCAGGTGCAGCTGCAGCAGCC
                                                 PstI FIBRE21FOR        --fibre----------/--scFv-------
                   L   S   F   D   S   T   Q   V   Q   L   Q
                  GCCTTAGTTTTGACAGCACACAGGTGCAGCTGCAGCAGCC
                                                  PstI FIBRE22FOR        --fibre----------/--scFv-------
           G   N   K   N   N   D   K   L   T   L   Q   V   Q   L   Q
          GGAAACAAAAATAATGATAAGCTAACTTTGCAGGTGCAGCTGCAGCAGCC
                                                       PstI FIBREPFOR         --fibre----------
                   Y   I   A   Q   E   *
                  CATACATTGCCCAAGAATAACAGGTGCAGCTGCAGCAGCCTGG
                                                    PstI
```

FIGURE 12B

```
              10        20        30        40        50
                                            M  K  Y  L  P
AAGCTTGCATGCAAATTCTATTTCAAGGAGACAGTCATAATGAAATACCTATTGCCT
HindIIISphI            SD                 /---------------

60        70        80        90       100       110
 T  A  A  A  G  L  L  L  L  A  A  Q  P  A  M  A  Q  V  Q
ACGGCAGCCGCTGGATTGTTATTACTCGCTGCCCAACCAGCGATGGCCCAGGTGCAG
------pelB leader----------------------------/VH_NP 120       130       140       150       160       170
 L  Q  Q  P  G  A  E  L  V  K  P  G  A  S  V  K  L  S  C
CTGCAGCAGCCTGGGGCTGAGCTTGTGAAGCCTGGGGCTTCAGTGAAGCTGTCCTGC
PstI 180       190       200       210       220        2
 K  A  S  G  Y  T  F  T  S  Y  W  M  H  W  V  K  Q  R  P
AAGGCTTCTGGCTACACCTTCACCAGCTACTGGATGCACTGGGTGAAGCAGAGGCCT
                          CDR1

30        240       250       260       270       280
 G  R  G  L  E  W  I  G  R  I  D  P  N  S  G  G  T  R  Y
GGACGAGGCCTTGAGTGGATTGGAAGGATTGATCCTAATAGTGGTGGTACTAAGTAC
                        CDR2

290       300       310       320       330       340
 N  E  K  F  L  S  K  A  T  L  T  V  D  K  P  S  S  T  A
AATGAGAAGTTCAAGAGCAAGGCCACACTGACTGTAGACAAACCCTCCAGCACAGCC 350       360       370       380       390        40
 Y  M  Q  L  S  S  L  T  S  E  D  S  A  V  Y  Y  C  A  R
TACATGCAGCTCAGCAGCCTGACATCTGAGGACTCTGCGGTCTATTATTGTGCAAGA 0        410       420       430       440       450
 Y  D  Y  Y  G  S  S  Y  F  D  Y  W  G  Q  G  T  T  L  T
TACGATTACTACGGTAGTAGCTACTTTGACTACTGGGGCCAAGGGACCACGGTCACC
         CDR3                                       BstEII 460       470       480       490       500       510
 V  S  S  G  G  G  G  S  G  G  G  G  S  G  G  G  G  S  Q
GTCTCCTCAGGTGGAGGCGGTTCAGGCGGAGGTGGCTCTGGCGGTGGCGGATCCCAG
       /-----------(G_4s)_3 linker--------------BamH1-IVλ
```

FIGURE 13A

```
        520       530       540       550       560       570
  V  V  L  T  Q  E  S  A  L  T  T  S  P  G  E  T  V  T  L
GCTGTTGTGACTCAGGAATCTGCACTCACCACATCACCTGGTGAAACAGTCACACTC 580       590       600       610       620
  T  C  R  S  S  T  G  A  V  T  T  S  N  Y  A  N  W  V  Q
ACTTGTCGCTCAAGTACTGGGGCTGTTACAACTAGTAACTATGCCAACTGGGTCCAA
              CDR1

630       640       650       660       670       680
  E  K  P  D  H  L  F  T  G  L  I  G  G  T  N  N  R  A  P
GAAAAACCAGATCATTTATTCACTGGTCTAATAGGTGGTACCAACAACCGAGCTCCA
                                       KpnI  CDR2    SstI 690       700       710       720       730       740
  G  V  P  A  R  F  S  G  S  L  I  G  D  K  A  A  L  T  I
GGTGTTCCTGCCAGATTCTCAGGCTCCCTGATTGGAGACAAGGCTGCCCTCACCATC 750       760       770       780       790      8
  T  G  A  Q  T  E  D  E  A  I  Y  F  C  A  L  W  Y  S  N
ACAGGGGCACAGACTGAGGATGAGGCAATATATTTCTGTGCTCTATGGTACAGCAAC
                                             CDR3

00       810       820       830       840       850
  H  W  V  F  G  G  G  T  K  L  T  V  L  G  L  E
CACTGGGTGTTCGGTGGAGGAACCAAACTGACTGTCCTAGGTCTCGAGTAATAAGAA
                                          XhoI        Eco

TTC
RI
```

FIGURE 13B

```
                    1                    5                10                   15               20
              Q  V  Q  L  Q  Q  S  G  A  E  L  M  K  P  G  A  S  V  K  I
MoVH-HMFG1    CAGGTTCAGCTGCAGCAGTCTGGAGCTGACCTGATGAAGCCTGGGGCCTCAGTGAAGATA
HuVH-HMFG1    CAGGTGCAGCTGGTGCAGTCTGGGGCAGGTGCAGGTGAAAAAGCCTGGGGCCTCAGTGAAGGTG
              Q  V  Q  L  Y  Q  S  G  A  E  Y  K  K  P  G  A  S  V  K  Y 25                    30      CDRL    35                 40
              S  C  K  A  T  G  Y  T  F  S  | A  Y  W  I  E |  W  V  K  Q  R
MoVH-HMFG1    TCCTGCAAGGCTACTGGCTACACATTCAGTGCCTACTGGATAGAGTGGGTAAAGCAGACC
Hu-VHHMFG1    TCCTGCAAGGCTTCTGGCTACACCTTCAGTGCCTACTGGATAGAGTGGGTGCGCCAGGCT
              S  C  K  A  S  G  Y  T  F  S  | A  Y  W  I  E |  W  V  B  Q  A 45                    50   52 A             55   CDR2
              P  G  H  G  L  E  W  I  G  | E  I  L  P  G  S  N  N  S  R  Y |
MoVH-HMFG1    CCTGGACATGGCCTTGAGTGGATTGGAGAGATTTTACCTGGAAGTAATAATTCTAGATAC
HuVH-HMFG1    CCAGGAAAAGGGCCTCGAGTGGGTCGGAGAGATTTTACCTGGAACTAATAATTCTAGATAC
              P  G  K  G  L  E  W  Y  G  | E  I  L  P  G  S  N  N  S  R  Y |
```

```
          60    CDR2         65                    70                 75
            N   E   K   F   K   G   K   A   T   F   T   A   D   T   S   S   N   T   A   Y
MoVH-HMFG1  AATGAGAAGTTCAAGGGCAAGGCCACATTCACTGCTGATACATCCTCCAACACAGCCTAC
HuVH-HMFG1  AATGAGAAGTTCAAGGGCCGAGTGACAGTCACTAGAGACACATCCACAAACACAGCCTAC
            N   E   K   F   K   G   R   V   T   V   T   B   D   T   S   I   N   T   A   Y 80  82 A B C                      85                    90                     95
            M   Q   L   S   S   L   T   S   E   D   S   A   V   Y   Y   C   S   R   S   Y
MoVH-HMFG1  ATGCAACTCAGCAGCCTGACATCTGAGGACTCTGCCGTCTATTACTGTTCAAGGTCCTAC
HuVH-HMFG1  ATGGAGCTCAGCAGCCTGAGGTCTGAGGACACAGCCGTCTATTACTGTTCCAAGATCCTAC
            M   E   L   S   S   L   B   S   E   D   I   A   V   Y   Y   C   B   R   S   Y

CDR3  100 A                              105                    110
            D   F   A   W   F   A   Y   W   G   Q   G   T   P   V   T   V   S   A
MoVH-HMFG1  GACTTTGCCTGGTTTGCTTACTGGGGCCAAGGGACTCCGGTCACTGTCTCTGCA
HuVH-HMFG1  GACTTTGCCTGGTTTGCTTACTGGGGCCAAGGGACTCTGGTCACAGTCTCCTCA
            D   F   A   W   F   A   Y   W   G   Q   G   T   L   V   T   V   S   S
```

```
                   1                  5                   10                  15                  20
              D   I   V   M   S   Q   S   P   S   S   L   A   V   S   V   G   E   K   V   T
MoVK-HMFG1    GACATTGTGATGTCACAGTCTCCATCCTCCCTAGCTGTGTCAGTTGGAGAGAAGGTTACT
HuVK-HMFG1    GACATCCAGATGACCCAGTCTCCAAGCAGCCTGAGCGCCTCTGTGGGTGACAGAGTGACC
              D   I   Q   M   T   Q   S   P   S   S   L   S   A   S   V   G   D   R   V   T 25          27  A   B   C   D   E   F           30    CDR1
              M   S   C   | K   S   S   Q   S   L   L   Y   S   N   Q   K   I   Y   L   A |
MoVK-HMFG1    ATGAGCTGC AAGTCCAGTCAGAGCCTTTTATATAGTAATCAAAAGATCTACTTGGCC
HuVK-HMFG1    ATCACCTGT AAGTCCAGTCAGAGCCTTTTATATAGTAATCAAAAGATCTACTTGGCC
              I   T   C   | K   S   S   Q   S   L   L   Y   S   N   Q   K   I   Y   L   A |

35                  40                  45                  50    CDR2
              W   Y   Q   Q   K   P   G   Q   S   P   K   L   L   I   Y   | W   A   S   T   R |
MoVK-HMFG1    TGGTACCAGCAGAAACCAGGGCAGTCTCCTAAACTGCTGATTTACTGGGCATCCACTAGG
HuVK-HMFG1    TGGTACCAGCAGAAGCCAGGTAAGGCTCCAAAGCTGCTGATCATCTACTGGGCATCCACTAGG
              W   Y   Q   Q   R   P   G   K   B   P   K   L   L   I   Y   | W   A   S   T   R |
```

```
              55                60                      65                       70
              E   S   G   V   P   P   D   R   F   T   G   G   G   S   G   T   D   F   T   L   T
MoVK-HMFG1    GAATCTGGGGTCCCTGATCGCTTCGCTTCACAGGCGGTGGATCTGGGACAGATTTCACTCTCACC
HuVK-HMFG1    GAATCTGGTGTGCCAAGCAGATTCAGCGGTAGCGGGTAGCGGTACCGACTTCACCTTCACC
              E   S   G   V   P   S   R   F   S   G   S   G   S   G   T   D   F   T   F   T   T 75                80                      85                  90  CDR3
              I   S   S   V   K   A   E   D   L   A   V   Y   Y   C   Q   Q   Y   Y   R   Y
MoVK-HMFG1    ATCAGCAGTGTGAAGGCTGAAGACCTGGCAGTTTATTACTGTCAGCAATATTATAGATAT
HuVK-HMFG1    ATCAGCAGCCTCCAGCCTGAAGACCAGCCGCCACCTACTGCCAGCAATATTATAGATAT
              I   S   S   L   Q   P   E   D   I   A   I   Y   Y   C   Q   Q   Y   Y   R   Y 95                100                     105
              P   R   T   F   G   G   G   T   K   L   E   I   K   R
MoVK-HMFG1    CCTCGGACGTTCGGTGGAGGCACCAAGCTGGAAATCAAACGG
HuVK-HMFG1    CCTCGGACGTTCGGCCAAGGGACCAAGGTGGAAATCAAACGT
              P   F   T   F   C   Q   G   T   K   V   E   I   K   R
```

FIGURE 15D

SEQUENCE LISTING ( 1 ) GENERAL INFORMATION:

( i i i ) NUMBER OF SEQUENCES: 80

( 2 ) INFORMATION FOR SEQ ID NO: 1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( i x ) FEATURE:
        ( A ) NAME/KEY: CDS
        ( B ) LOCATION: 1..30

( x i ) SEQUENCE DESCRIPTION: SEQ ID NO: 1:

```
CCT  CTA  GTT  ACC  TCC  AAT  GTG  CAG  CTG  CAG                              30
Pro  Leu  Val  Thr  Ser  Asn  Val  Gln  Leu  Gln
 1              5                        10
```

( 2 ) INFORMATION FOR SEQ ID NO: 2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Pro  Leu  Val  Thr  Ser  Asn  Val  Gln  Leu  Gln
 1              5                        10
```

( 2 ) INFORMATION FOR SEQ ID NO: 3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( i x ) FEATURE:
        ( A ) NAME/KEY: CDS
        ( B ) LOCATION: 1..30

( x i ) SEQUENCE DESCRIPTION: SEQ ID NO: 3:

```
CTC  TCT  CTG  GAC  GAG  GCC  GTG  CAG  CTG  CAG                              30
Leu  Ser  Leu  Asp  Glu  Ala  Val  Gln  Leu  Gln
 1              5                        10
```

( 2 ) INFORMATION FOR SEQ ID NO: 4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Leu  Ser  Leu  Asp  Glu  Ala  Val  Gln  Leu  Gln
 1              5                         10
```

( 2 ) INFORMATION FOR SEQ ID NO: 5:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( i x ) FEATURE:
        ( A ) NAME/KEY: CDS
        ( B ) LOCATION: 1..30

( x i ) SEQUENCE DESCRIPTION: SEQ ID NO: 5:

```
CCT  CTC  AAA  AAA  ACC  AAG  GTG  CAG  CTG  CAG                    30
Pro  Leu  Lys  Lys  Thr  Lys  Val  Gln  Leu  Gln
 1              5                         10
```

( 2 ) INFORMATION FOR SEQ ID NO: 6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Pro  Leu  Lys  Lys  Thr  Lys  Val  Gln  Leu  Gln
 1              5                         10
```

( 2 ) INFORMATION FOR SEQ ID NO: 7:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( i x ) FEATURE:
        ( A ) NAME/KEY: CDS (B) LOCATION: 1..30

(x i) SEQUENCE DESCRIPTION: SEQ ID NO: 7:

| CCC | CTC | ACA | GTT | ACC | TCA | GTG | CAG | CTG | CAG | 30 |
|---|---|---|---|---|---|---|---|---|---|---|
| Pro | Leu | Thr | Val | Thr | Ser | Val | Gln | Leu | Gln | |
| 1 | | | | 5 | | | | | 10 | |

(2) INFORMATION FOR SEQ ID NO: 8:

(i) SEQUENCE CHARACTERISTICS:
        (A) LENGTH: 10 amino acids
        (B) TYPE: amino acid
        (D) TOPOLOGY: linear (i i) MOLECULE TYPE: protein (x i) SEQUENCE DESCRIPTION: SEQ ID NO: 8:

| Pro | Leu | Thr | Val | Thr | Ser | Val | Gln | Leu | Gln |
|---|---|---|---|---|---|---|---|---|---|
| 1 | | | | 5 | | | | | 10 |

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
        (A) ORGANISM: Adenovirus
        (B) STRAIN: Ad5

(i x) FEATURE:
        (A) NAME/KEY: CDS
        (B) LOCATION: 1..30

(x i) SEQUENCE DESCRIPTION: SEQ ID NO: 9:

| CCT | CTA | ATG | GTC | GCG | GGC | GTG | CAG | CTG | CAG | 30 |
|---|---|---|---|---|---|---|---|---|---|---|
| Pro | Leu | Met | Val | Ala | Gly | Val | Gln | Leu | Gln | |
| 1 | | | | 5 | | | | | 10 | |

(2) INFORMATION FOR SEQ ID NO: 10:

(i) SEQUENCE CHARACTERISTICS:
        (A) LENGTH: 10 amino acids
        (B) TYPE: amino acid
        (D) TOPOLOGY: linear (i i) MOLECULE TYPE: protein (x i) SEQUENCE DESCRIPTION: SEQ ID NO: 10:

| Pro | Leu | Met | Val | Ala | Gly | Val | Gln | Leu | Gln |
|---|---|---|---|---|---|---|---|---|---|
| 1 | | | | 5 | | | | | 10 |

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
  (A) ORGANISM: Adenovirus
  (B) STRAIN: Ad5

(i x) FEATURE:
  (A) NAME/KEY: CDS
  (B) LOCATION: 1..30

(x i) SEQUENCE DESCRIPTION: SEQ ID NO: 11:

```
CCG CTA ACC GTG CAC GAC GTG CAG CTG CAG                    30
Pro Leu Thr Val His Asp Val Gln Leu Gln
 1               5                  10
```

(2) INFORMATION FOR SEQ ID NO: 12:

(i) SEQUENCE CHARACTERISTICS:
    (A) LENGTH: 10 amino acids
    (B) TYPE: amino acid
    (D) TOPOLOGY: linear (i i) MOLECULE TYPE: protein (x i) SEQUENCE DESCRIPTION: SEQ ID NO: 12:

```
Pro Leu Thr Val His Asp Val Gln Leu Gln
 1               5                  10
```

(2) INFORMATION FOR SEQ ID NO: 13:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
    (A) ORGANISM: Adenovirus
    (B) STRAIN: Ad5

(i x) FEATURE:
    (A) NAME/KEY: CDS
    (B) LOCATION: 1..30

(x i) SEQUENCE DESCRIPTION: SEQ ID NO: 13:

```
CCC CTC ACA GTG TCA GAA GTG CAG CTG CAG                    30
Pro Leu Thr Val Ser Glu Val Gln Leu Gln
 1               5                  10
```

(2) INFORMATION FOR SEQ ID NO: 14:

(i) SEQUENCE CHARACTERISTICS:
    (A) LENGTH: 10 amino acids
    (B) TYPE: amino acid
    (D) TOPOLOGY: linear (i i) MOLECULE TYPE: protein (x i) SEQUENCE DESCRIPTION: SEQ ID NO: 14:

```
Pro Leu Thr Val Ser Glu Val Gln Leu Gln
 1               5                  10
```

(2) INFORMATION FOR SEQ ID NO: 15:

(i) SEQUENCE CHARACTERISTICS:
    (A) LENGTH: 30 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Adenovirus
(B) STRAIN: Ad5

(ix) FEATURE:
(A) NAME/KEY: CDS
(B) LOCATION: 1..30

(xi) SEQUENCE DESCRIPTION: SEQ ID NO: 15:

```
CTC  ACC  ACC  ACC  GAT  AGC  GTG  CAG  CTG  CAG                30
Leu  Thr  Thr  Thr  Asp  Ser  Val  Gln  Leu  Gln
 1                   5                        10
```

(2) INFORMATION FOR SEQ ID NO: 16:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 16:

```
Leu  Thr  Thr  Thr  Asp  Ser  Val  Gln  Leu  Gln
 1                   5                        10
```

(2) INFORMATION FOR SEQ ID NO: 17:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Adenovirus
(B) STRAIN: Ad5

(ix) FEATURE:
(A) NAME/KEY: CDS
(B) LOCATION: 1..30

(xi) SEQUENCE DESCRIPTION: SEQ ID NO: 17:

```
CCT  CTA  ACT  ACT  GCC  ACT  GTG  CAG  CTG  CAG                30
Pro  Leu  Thr  Thr  Ala  Thr  Val  Gln  Leu  Gln
 1                   5                        10
```

(2) INFORMATION FOR SEQ ID NO: 18:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 18:

Pro Leu Thr Thr Ala Thr Val Gln Leu Gln
 1               5                   10

(2) INFORMATION FOR SEQ ID NO: 19:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Adenovirus
    (B) STRAIN: Ad5

(ix) FEATURE:
    (A) NAME/KEY: CDS
    (B) LOCATION: 1..30

(xi) SEQUENCE DESCRIPTION: SEQ ID NO: 19:

CCC ATT TAT ACA CAA AAT GTG CAG CTG CAG  30
Pro Ile Tyr Thr Gln Asn Val Gln Leu Gln
 1               5                   10

(2) INFORMATION FOR SEQ ID NO: 20:

(i) SEQUENCE CHARACTERISTICS:
    (A) LENGTH: 10 amino acids
    (B) TYPE: amino acid
    (D) TOPOLOGY: linear (ii) MOLECULE TYPE: protein (xi) SEQUENCE DESCRIPTION: SEQ ID NO: 20:

Pro Ile Tyr Thr Gln Asn Val Gln Leu Gln
 1               5                   10

(2) INFORMATION FOR SEQ ID NO: 21:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Adenovirus
    (B) STRAIN: Ad5

(ix) FEATURE:
    (A) NAME/KEY: CDS
    (B) LOCATION: 1..30

(xi) SEQUENCE DESCRIPTION: SEQ ID NO: 21:

CAT GTA ACA GAC GAC CTA GTG CAG CTG CAG  30
His Val Thr Asp Asp Leu Val Gln Leu Gln
 1               5                   10

(2) INFORMATION FOR SEQ ID NO: 22:

(i) SEQUENCE CHARACTERISTICS:

(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 22:

His Val Thr Asp Asp Leu Val Gln Leu Gln
 1               5                   10

(2) INFORMATION FOR SEQ ID NO: 23:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Adenovirus
(B) STRAIN: Ad5

(ix) FEATURE:
(A) NAME/KEY: CDS
(B) LOCATION: 1..30

(xi) SEQUENCE DESCRIPTION: SEQ ID NO: 23:

GGT GTG ACT ATT AAT AAT GTG CAG CTG CAG                    30
Gly Val Thr Ile Asn Asn Val Gln Leu Gln
 1               5                   10

(2) INFORMATION FOR SEQ ID NO: 24:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 24:

Gly Val Thr Ile Asn Asn Val Gln Leu Gln
 1               5                   10

(2) INFORMATION FOR SEQ ID NO: 25:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Adenovirus
(B) STRAIN: Ad5

(ix) FEATURE:
(A) NAME/KEY: CDS
(B) LOCATION: 1..30

(xi) SEQUENCE DESCRIPTION: SEQ ID NO: 25:

```
GGT  TTT  GAT  TCA  CAA  GGC  GTG  CAG  CTG  CAG                          30
Gly  Phe  Asp  Ser  Gln  Gly  Val  Gln  Leu  Gln
 1              5                        10
```

(2) INFORMATION FOR SEQ ID NO: 26:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 26:

```
Gly  Phe  Asp  Ser  Gln  Gly  Val  Gln  Leu  Gln
 1              5                        10
```

(2) INFORMATION FOR SEQ ID NO: 27:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Adenovirus
        (B) STRAIN: Ad5

(ix) FEATURE:
        (A) NAME/KEY: CDS
        (B) LOCATION: 1..30

(xi) SEQUENCE DESCRIPTION: SEQ ID NO: 27:

```
AGG  ATT  GAT  TCT  CAA  AAC  GTG  CAG  CTG  CAG                          30
Arg  Ile  Asp  Ser  Gln  Asn  Val  Gln  Leu  Gln
 1              5                        10
```

(2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 28:

```
Arg  Ile  Asp  Ser  Gln  Asn  Val  Gln  Leu  Gln
 1              5                        10
```

(2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Adenovirus (B) STRAIN: Ad5

(ix) FEATURE:
(A) NAME/KEY: CDS
(B) LOCATION: 1..30

(xi) SEQUENCE DESCRIPTION: SEQ ID NO: 29:

| TTT | GAT | GCT | CAA | AAC | CAA | GTG | CAG | CTG | CAG | 30 |
| Phe | Asp | Ala | Gln | Asn | Gln | Val | Gln | Leu | Gln | |
| 1   |     |     |     | 5   |     |     |     |     | 10  | |

(2) INFORMATION FOR SEQ ID NO: 30:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 30:

Phe Asp Ala Gln Asn Gln Val Gln Leu Gln
1               5                   10

(2) INFORMATION FOR SEQ ID NO: 31:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Adenovirus
(B) STRAIN: Ad5

(ix) FEATURE:
(A) NAME/KEY: CDS
(B) LOCATION: 1..30

(xi) SEQUENCE DESCRIPTION: SEQ ID NO: 31:

| CTT | TTT | ATA | AAC | TCA | GCC | GTG | CAG | CTG | CAG | 30 |
| Leu | Phe | Ile | Asn | Ser | Ala | Val | Gln | Leu | Gln | |
| 1   |     |     |     | 5   |     |     |     |     | 10  | |

(2) INFORMATION FOR SEQ ID NO: 32:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO: 32:

Leu Phe Ile Asn Ser Ala Val Gln Leu Gln
1               5                   10

(2) INFORMATION FOR SEQ ID NO: 33:

(i) SEQUENCE CHARACTERISTICS:
(A) LENGTH: 30 base pairs
(B) TYPE: nucleic acid
(C) STRANDEDNESS: double
(D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
  (A) ORGANISM: Adenovirus
  (B) STRAIN: Ad5

(i x) FEATURE:
  (A) NAME/KEY: CDS
  (B) LOCATION: 1..30

(x i) SEQUENCE DESCRIPTION: SEQ ID NO: 33:

| TCA | AAC | AAT | TCC | AAA | AAC | GTG | CAG | CTG | CAG | 30 |
| Ser | Asn | Asn | Ser | Lys | Asn | Val | Gln | Leu | Gln | |
| 1 | | | | 5 | | | | | 10 | |

(2) INFORMATION FOR SEQ ID NO: 34:

(i) SEQUENCE CHARACTERISTICS:
  (A) LENGTH: 10 amino acids
  (B) TYPE: amino acid
  (D) TOPOLOGY: linear (i i) MOLECULE TYPE: protein (x i) SEQUENCE DESCRIPTION: SEQ ID NO: 34:

Ser Asn Asn Ser Lys Asn Val Gln Leu Gln
1               5               10

(2) INFORMATION FOR SEQ ID NO: 35:

(i) SEQUENCE CHARACTERISTICS:
  (A) LENGTH: 30 base pairs
  (B) TYPE: nucleic acid
  (C) STRANDEDNESS: double
  (D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
  (A) ORGANISM: Adenovirus
  (B) STRAIN: Ad5

(i x) FEATURE:
  (A) NAME/KEY: CDS
  (B) LOCATION: 1..30

(x i) SEQUENCE DESCRIPTION: SEQ ID NO: 35:

| GGG | TTG | ATG | TTT | GAC | GCT | GTG | CAG | CTG | CAG | 30 |
| Gly | Leu | Met | Phe | Asp | Ala | Val | Gln | Leu | Gln | |
| 1 | | | | 5 | | | | | 10 | |

(2) INFORMATION FOR SEQ ID NO: 36:

(i) SEQUENCE CHARACTERISTICS:
  (A) LENGTH: 10 amino acids
  (B) TYPE: amino acid
  (D) TOPOLOGY: linear (i i) MOLECULE TYPE: protein (x i) SEQUENCE DESCRIPTION: SEQ ID NO: 36:

Gly Leu Met Phe Asp Ala Val Gln Leu Gln
1               5               10

( 2 ) INFORMATION FOR SEQ ID NO: 37:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( i x ) FEATURE:
        ( A ) NAME/KEY: CDS
        ( B ) LOCATION: 1..30

( x i ) SEQUENCE DESCRIPTION: SEQ ID NO: 37:

```
CCT  AAT  GCA  CCA  AAC  ACA  GTG  CAG  CTG  CAG                         30
Pro  Asn  Ala  Pro  Asn  Thr  Val  Gln  Leu  Gln
 1              5                        10
```

( 2 ) INFORMATION FOR SEQ ID NO: 38:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 38:

```
Pro  Asn  Ala  Pro  Asn  Thr  Val  Gln  Leu  Gln
 1              5                        10
```

( 2 ) INFORMATION FOR SEQ ID NO: 39:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( i x ) FEATURE:
        ( A ) NAME/KEY: CDS
        ( B ) LOCATION: 1..30

( x i ) SEQUENCE DESCRIPTION: SEQ ID NO: 39:

```
CTA  GAA  TTT  GAT  TCA  AAC  GTG  CAG  CTG  CAG                         30
Leu  Glu  Phe  Asp  Ser  Asn  Val  Gln  Leu  Gln
 1              5                        10
```

( 2 ) INFORMATION FOR SEQ ID NO: 40:

( i ) SEQUENCE CHARACTERISTICS:
        ( A ) LENGTH: 10 amino acids
        ( B ) TYPE: amino acid
        ( D ) TOPOLOGY: linear (i i) MOLECULE TYPE: protein (x i) SEQUENCE DESCRIPTION: SEQ ID NO: 40:

```
Leu Glu Phe Asp Ser Asn Val Gln Leu Gln
 1               5                  10
```

(2) INFORMATION FOR SEQ ID NO: 41:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
        (A) ORGANISM: Adenovirus
        (B) STRAIN: Ad5

(i x) FEATURE:
        (A) NAME/KEY: CDS
        (B) LOCATION: 1..30

(x i) SEQUENCE DESCRIPTION: SEQ ID NO: 41:

```
CTT AGT TTT GAC AGC ACA GTG CAG CTG CAG                      30
Leu Ser Phe Asp Ser Thr Val Gln Leu Gln
 1               5                  10
```

(2) INFORMATION FOR SEQ ID NO: 42:

(i) SEQUENCE CHARACTERISTICS:
        (A) LENGTH: 10 amino acids
        (B) TYPE: amino acid
        (D) TOPOLOGY: linear (i i) MOLECULE TYPE: protein (x i) SEQUENCE DESCRIPTION: SEQ ID NO: 42:

```
Leu Ser Phe Asp Ser Thr Val Gln Leu Gln
 1               5                  10
```

(2) INFORMATION FOR SEQ ID NO: 43:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i i i) ANTI-SENSE: NO (v i) ORIGINAL SOURCE:
        (A) ORGANISM: Adenovirus
        (B) STRAIN: Ad5

(i x) FEATURE:
        (A) NAME/KEY: CDS
        (B) LOCATION: 1..30

(x i) SEQUENCE DESCRIPTION: SEQ ID NO: 43:

```
ATT GAT AAG CTA ACT TTG GTG CAG CTG CAG                      30
Ile Asp Lys Leu Thr Leu Val Gln Leu Gln
 1               5                  10
```

( 2 ) INFORMATION FOR SEQ ID NO: 44:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 44:

```
Ile Asp Lys Leu Thr Leu Val Gln Leu Gln
 1               5                   10
```

( 2 ) INFORMATION FOR SEQ ID NO: 45:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Adenovirus
        ( B ) STRAIN: Ad5

( x i ) SEQUENCE DESCRIPTION: SEQ ID NO: 45:

CTCGAGTAAT AAGAATTC        18

( 2 ) INFORMATION FOR SEQ ID NO: 46:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 46:

AGCTAAGCTT GCATGCAAAT TC        22

( 2 ) INFORMATION FOR SEQ ID NO: 47:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 1..27

( x i ) SEQUENCE DESCRIPTION: SEQ ID NO: 47:

```
CCA GCG ATG GCC AGA TCT CAG CTG CAG AGCT       31
Pro Ala Met Ala Arg Ser Gln Leu Gln
```

( 2 ) INFORMATION FOR SEQ ID NO: 48:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 48:

```
Pro  Ala  Met  Ala  Arg  Ser  Gln  Leu  Gln
  1                  5
```

( 2 ) INFORMATION FOR SEQ ID NO: 49:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 40..132

( x i ) SEQUENCE DESCRIPTION: SEQ ID NO: 49:

```
AAGCTTGCAT  GCAAATTCTA  TTTCAAGGAG  ACAGTCATA ATG AAA TAC CTA TTG         54
                                              Met Lys Tyr Leu Leu
                                                1               5

CCT ACG GCA GCC GCT GGA TTG TTA TTA CTC GCT GCC CAA CCA GCG ATG         102
Pro Thr Ala Ala Ala Gly Leu Leu Leu Leu Ala Ala Gln Pro Ala Met
             10                  15                  20

GCC AGA TCT CAG CTG CAG GTC GAC GGA TCC                                 132
Ala Arg Ser Gln Leu Gln Val Asp Gly Ser
         25                  30
```

( 2 ) INFORMATION FOR SEQ ID NO: 50:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 50:

```
Met Lys Tyr Leu Leu Pro Thr Ala Ala Ala Gly Leu Leu Leu Leu Ala
  1               5                  10                  15
Ala Gln Pro Ala Met Ala Arg Ser Gln Leu Gln Val Asp Gly Ser
             20                  25                  30
```

( 2 ) INFORMATION FOR SEQ ID NO: 51:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (i i i) ANTI-SENSE: NO (i x) FEATURE:
 (A) NAME/KEY: CDS
 (B) LOCATION: 5..28

(x i) SEQUENCE DESCRIPTION: SEQ ID NO: 51:

```
AGCT AGA TCT ATG AAG CGC GCA AGA CCG                    28
     Arg Ser Met Lys Arg Ala Arg Pro
      1               5
```

(2) INFORMATION FOR SEQ ID NO: 52:

(i) SEQUENCE CHARACTERISTICS:
  (A) LENGTH: 8 amino acids
  (B) TYPE: amino acid
  (D) TOPOLOGY: linear (i i) MOLECULE TYPE: protein (x i) SEQUENCE DESCRIPTION: SEQ ID NO: 52:

```
Arg Ser Met Lys Arg Ala Arg Pro
 1               5
```

(2) INFORMATION FOR SEQ ID NO: 53:

(i) SEQUENCE CHARACTERISTICS:
  (A) LENGTH: 41 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (i i i) ANTI-SENSE: NO (i x) FEATURE:
  (A) NAME/KEY: CDS
  (B) LOCATION: 1..33

(x i) SEQUENCE DESCRIPTION: SEQ ID NO: 53:

```
CCT CTC AAA AAA ACC AAG CAG GTG CAG CTG CAG CAGCCTGG    41
Pro Leu Lys Lys Thr Lys Gln Val Gln Leu Gln
 1               5                   10
```

(2) INFORMATION FOR SEQ ID NO: 54:

(i) SEQUENCE CHARACTERISTICS:
  (A) LENGTH: 11 amino acids
  (B) TYPE: amino acid
  (D) TOPOLOGY: linear (i i) MOLECULE TYPE: protein (x i) SEQUENCE DESCRIPTION: SEQ ID NO: 54:

```
Pro Leu Lys Lys Thr Lys Gln Val Gln Leu Gln
 1               5                   10
```

(2) INFORMATION FOR SEQ ID NO: 55:

(i) SEQUENCE CHARACTERISTICS:
  (A) LENGTH: 42 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO ( i i i ) ANTI-SENSE: NO ( i x ) FEATURE:
(A) NAME/KEY: CDS
(B) LOCATION: 2..34

( x i ) SEQUENCE DESCRIPTION: SEQ ID NO: 55:

```
C CCG CTA ACC GTG CAC GAC CAG GTG CAG CTG CAG CAGCCTGG        42
  Pro Leu Thr Val His Asp Gln Val Gln Leu Gln
  1               5                   10
```

( 2 ) INFORMATION FOR SEQ ID NO: 56:

(i) SEQUENCE CHARACTERISTICS:
(A) LENGTH: 11 amino acids
(B) TYPE: amino acid
(D) TOPOLOGY: linear (ii) MOLECULE TYPE: protein ( x i ) SEQUENCE DESCRIPTION: SEQ ID NO: 56:

```
Pro Leu Thr Val His Asp Gln Val Gln Leu Gln
1               5                   10
```

( 2 ) INFORMATION FOR SEQ ID NO: 57:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

( i i i ) HYPOTHETICAL: NO ( i i i ) ANTI-SENSE: NO ( i x ) FEATURE:
(A) NAME/KEY: CDS
(B) LOCATION: 1..33

( x i ) SEQUENCE DESCRIPTION: SEQ ID NO: 57:

```
CCT CTA ACT ACT GCC ACT CAG GTG CAG CTG CAG CAGCCTGG          41
Pro Leu Thr Thr Ala Thr Gln Val Gln Leu Gln
1               5                   10
```

( 2 ) INFORMATION FOR SEQ ID NO: 58:

(i) SEQUENCE CHARACTERISTICS:
(A) LENGTH: 11 amino acids
(B) TYPE: amino acid
(D) TOPOLOGY: linear (ii) MOLECULE TYPE: protein ( x i ) SEQUENCE DESCRIPTION: SEQ ID NO: 58:

```
Pro Leu Thr Thr Ala Thr Gln Val Gln Leu Gln
1               5                   10
```

( 2 ) INFORMATION FOR SEQ ID NO: 59:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

( i i i ) HYPOTHETICAL: NO ( i i i ) ANTI-SENSE: NO ( i x ) FEATURE:
    ( A ) NAME/KEY: CDS
    ( B ) LOCATION: 1..33

( x i ) SEQUENCE DESCRIPTION: SEQ ID NO: 59:

```
GGT  GTG  ACT  ATT  AAT  AAT  CAG  GTG  CAG  CTG  CAG  GACCCTGG       41
Gly  Val  Thr  Ile  Asn  Asn  Gln  Val  Gln  Leu  Gln
 1                  5                        10
```

( 2 ) INFORMATION FOR SEQ ID NO: 60:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 60:

```
Gly  Val  Thr  Ile  Asn  Asn  Gln  Val  Gln  Leu  Gln
 1                  5                        10
```

( 2 ) INFORMATION FOR SEQ ID NO: 61:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 1..36

( x i ) SEQUENCE DESCRIPTION: SEQ ID NO: 61:

```
CCG  TTT  GAT  GCT  CAA  AAC  CAA  CAG  GTG  CAG  CTG  CAG  CAGCC    41
Pro  Phe  Asp  Ala  Gln  Asn  Gln  Gln  Val  Gln  Leu  Gln
 1                  5                        10
```

( 2 ) INFORMATION FOR SEQ ID NO: 62:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 62:

```
Pro  Phe  Asp  Ala  Gln  Asn  Gln  Gln  Val  Gln  Leu  Gln
 1                  5                        10
```

( 2 ) INFORMATION FOR SEQ ID NO: 63:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
  ( A ) NAME/KEY: CDS
  ( B ) LOCATION: 1..33

( x i ) SEQUENCE DESCRIPTION: SEQ ID NO: 63:

```
GGG  TTG  ATG  TTT  GAC  GCT  CAG  GTG  CAG  CTG  CAG  CAGCC           38
Gly  Leu  Met  Phe  Asp  Ala  Gln  Val  Gln  Leu  Gln
 1                   5                        10
```

( 2 ) INFORMATION FOR SEQ ID NO: 64:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 64:

```
Gly  Leu  Met  Phe  Asp  Ala  Gln  Val  Gln  Leu  Gln
 1                   5                        10
```

( 2 ) INFORMATION FOR SEQ ID NO: 65:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
    ( A ) NAME/KEY: CDS
    ( B ) LOCATION: 3..35

( x i ) SEQUENCE DESCRIPTION: SEQ ID NO: 65:

```
GC  CTT  AGT  TTT  GAC  AGC  ACA  CAG  GTG  CAG  CTG  CAG  CAGCC       40
    Leu  Ser  Phe  Asp  Ser  Thr  Gln  Val  Gln  Leu  Gln
     1                   5                        10
```

( 2 ) INFORMATION FOR SEQ ID NO: 66:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 66:

```
Leu  Ser  Phe  Asp  Ser  Thr  Gln  Val  Gln  Leu  Gln
 1                   5                        10
```

( 2 ) INFORMATION FOR SEQ ID NO: 67:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
(A) NAME/KEY: CDS
(B) LOCATION: 1..45

( x i ) SEQUENCE DESCRIPTION: SEQ ID NO: 67:

| GGA | AAC | AAA | AAT | AAT | GAT | AAG | CTA | ACT | TTG | CAG | GTG | CAG | CTG | CAG | 45 |
|---|---|---|---|---|---|---|---|---|---|---|---|---|---|---|---|
| Gly | Asn | Lys | Asn | Asn | Asp | Lys | Leu | Thr | Leu | Gln | Val | Gln | Leu | Gln | |
| 1 | | | | 5 | | | | | 10 | | | | | 15 | |

CAGCC    50

(2) INFORMATION FOR SEQ ID NO: 68:

( i ) SEQUENCE CHARACTERISTICS:
(A) LENGTH: 15 amino acids
(B) TYPE: amino acid
(D) TOPOLOGY: linear ( i i ) MOLECULE TYPE: protein ( x i ) SEQUENCE DESCRIPTION: SEQ ID NO: 68:

| Gly | Asn | Lys | Asn | Asn | Asp | Lys | Leu | Thr | Leu | Gln | Val | Gln | Leu | Gln |
|---|---|---|---|---|---|---|---|---|---|---|---|---|---|---|
| 1 | | | | 5 | | | | | 10 | | | | | 15 |

(2) INFORMATION FOR SEQ ID NO: 69:

( i ) SEQUENCE CHARACTERISTICS:
(A) LENGTH: 43 base pairs
(B) TYPE: nucleic acid
(C) STRANDEDNESS: single
(D) TOPOLOGY: linear ( i i ) MOLECULE TYPE: DNA (genomic)

( i i i ) HYPOTHETICAL: NO ( i i i ) ANTI-SENSE: NO ( i x ) FEATURE:
(A) NAME/KEY: CDS
(B) LOCATION: 3..17

( x i ) SEQUENCE DESCRIPTION: SEQ ID NO: 69:

| CA | TAC | ATT | GCC | CAA | GAA | TAACAGGTGC | AGCTGCAGCA | GCCTGG | 43 |
|---|---|---|---|---|---|---|---|---|---|
| | Tyr | Ile | Ala | Gln | Glu | | | | |
| | 1 | | | | 5 | | | | |

(2) INFORMATION FOR SEQ ID NO: 70:

( i ) SEQUENCE CHARACTERISTICS:
(A) LENGTH: 5 amino acids
(B) TYPE: amino acid
(D) TOPOLOGY: linear ( i i ) MOLECULE TYPE: protein ( x i ) SEQUENCE DESCRIPTION: SEQ ID NO: 70:

| Tyr | Ile | Ala | Gln | Glu |
|---|---|---|---|---|
| 1 | | | | 5 |

(2) INFORMATION FOR SEQ ID NO: 71:

( i ) SEQUENCE CHARACTERISTICS:
(A) LENGTH: 858 base pairs
(B) TYPE: nucleic acid
(C) STRANDEDNESS: double
(D) TOPOLOGY: linear ( i i ) MOLECULE TYPE: DNA (genomic)

( i i i ) HYPOTHETICAL: NO ( i i i ) ANTI-SENSE: NO ( i x ) FEATURE:
    ( A ) NAME/KEY: CDS
    ( B ) LOCATION: 40..846

( x i ) SEQUENCE DESCRIPTION: SEQ ID NO: 71:

```
AAGCTTGCAT GCAAATTCTA TTTCAAGGAG ACAGTCATA ATG AAA TAC CTA TTG        54
                                            Met Lys Tyr Leu Leu
                                             1               5

CCT ACG GCA GCC GCT GGA TTG TTA TTA CTC GCT GCC CAA CCA GCG ATG      102
Pro Thr Ala Ala Ala Gly Leu Leu Leu Leu Ala Ala Gln Pro Ala Met
             10                  15                  20

GCC CAG GTG CAG CTG CAG CAG CCT GGG GCT GAG CTT GTG AAG CCT GGG      150
Ala Gln Val Gln Leu Gln Gln Pro Gly Ala Glu Leu Val Lys Pro Gly
         25                  30                  35

GCT TCA GTG AAG CTG TCC TGC AAG GCT TCT GGC TAC ACC TTC ACC AGC      198
Ala Ser Val Lys Leu Ser Cys Lys Ala Ser Gly Tyr Thr Phe Thr Ser
             40                  45                  50

TAC TGG ATG CAC TGG GTG AAG CAG AGG CCT GGA CGA GGC CTT GAG TGG      246
Tyr Trp Met His Trp Val Lys Gln Arg Pro Gly Arg Gly Leu Glu Trp
     55                  60                  65

ATT GGA AGG ATT GAT CCT AAT AGT GGT GGT ACT AAG TAC AAT GAG AAG      294
Ile Gly Arg Ile Asp Pro Asn Ser Gly Gly Thr Lys Tyr Asn Glu Lys
 70                  75                  80                  85

TTC AAG AGC AAG GCC ACA CTG ACT GTA GAC AAA CCC TCC AGC ACA GCC      342
Phe Lys Ser Lys Ala Thr Leu Thr Val Asp Lys Pro Ser Ser Thr Ala
                 90                  95                 100

TAC ATG CAG CTC AGC AGC CTG ACA TCT GAG GAC TCT GCG GTC TAT TAT      390
Tyr Met Gln Leu Ser Ser Leu Thr Ser Glu Asp Ser Ala Val Tyr Tyr
             105                 110                 115

TGT GCA AGA TAC GAT TAC TAC GGT AGT AGC TAC TTT GAC TAC TGG GGC      438
Cys Ala Arg Tyr Asp Tyr Tyr Gly Ser Ser Tyr Phe Asp Tyr Trp Gly
         120                 125                 130

CAA GGG ACC ACG GTC ACC GTC TCC TCA GGT GGA GGC GGT TCA GGC GGA      486
Gln Gly Thr Thr Val Thr Val Ser Ser Gly Gly Gly Gly Ser Gly Gly
     135                 140                 145

GGT GGC TCT GGC GGT GGC GGA TCC CAG GCT GTT GTG ACT CAG GAA TCT      534
Gly Gly Ser Gly Gly Gly Gly Ser Gln Ala Val Val Thr Gln Glu Ser
150                 155                 160                 165

GCA CTC ACC ACA TCA CCT GGT GAA ACA GTC ACA CTC ACT TGT CGC TCA      582
Ala Leu Thr Thr Ser Pro Gly Glu Thr Val Thr Leu Thr Cys Arg Ser
                 170                 175                 180

AGT ACT GGG GCT GTT ACA ACT AGT AAC TAT GCC AAC TGG GTC CAA GAA      630
Ser Thr Gly Ala Val Thr Thr Ser Asn Tyr Ala Asn Trp Val Gln Glu
             185                 190                 195

AAA CCA GAT CAT TTA TTC ACT GGT CTA ATA GGT GGT ACC AAC AAC CGA      678
Lys Pro Asp His Leu Phe Thr Gly Leu Ile Gly Gly Thr Asn Asn Arg
         200                 205                 210

GCT CCA GGT GTT CCT GCC AGA TTC TCA GGC TCC CTG ATT GGA GAC AAG      726
Ala Pro Gly Val Pro Ala Arg Phe Ser Gly Ser Leu Ile Gly Asp Lys
     215                 220                 225

GCT GCC CTC ACC ATC ACA GGG GCA CAG ACT GAG GAT GAG GCA ATA TAT      774
Ala Ala Leu Thr Ile Thr Gly Ala Gln Thr Glu Asp Glu Ala Ile Tyr
230                 235                 240                 245

TTC TGT GCT CTA TGG TAC AGC AAC CAC TGG GTG TTC GGT GGA GGA ACC      822
Phe Cys Ala Leu Trp Tyr Ser Asn His Trp Val Phe Gly Gly Gly Thr
                 250                 255                 260

AAA CTG ACT GTC CTA GGT CTC GAG TAATAAGAAT TC                        858
```

Lys Leu Thr Val Leu Gly Leu Glu
            265

(2) INFORMATION FOR SEQ ID NO: 72:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO: 72:

Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln Gln Pro Gly Ala Glu
            20                  25                  30

Leu Val Lys Pro Gly Ala Ser Val Lys Leu Ser Cys Lys Ala Ser Gly
            35                  40                  45

Tyr Thr Phe Thr Ser Tyr Trp Met His Trp Val Lys Gln Arg Pro Gly
     50                  55                  60

Arg Gly Leu Glu Trp Ile Gly Arg Ile Asp Pro Asn Ser Gly Gly Thr
65                   70                  75                  80

Lys Tyr Asn Glu Lys Phe Lys Ser Lys Ala Thr Leu Thr Val Asp Lys
                85                  90                  95

Pro Ser Ser Thr Ala Tyr Met Gln Leu Ser Ser Leu Thr Ser Glu Asp
            100                 105                 110

Ser Ala Val Tyr Tyr Cys Ala Arg Tyr Asp Tyr Tyr Gly Ser Ser Tyr
            115                 120                 125

Phe Asp Tyr Trp Gly Gln Gly Thr Thr Val Thr Val Ser Ser Gly Gly
     130                 135                 140

Gly Gly Ser Gly Gly Gly Gly Ser Gly Gly Gly Gly Ser Gln Ala Val
145                 150                 155                 160

Val Thr Gln Glu Ser Ala Leu Thr Thr Ser Pro Gly Glu Thr Val Thr
                165                 170                 175

Leu Thr Cys Arg Ser Ser Thr Gly Ala Val Thr Thr Ser Asn Tyr Ala
            180                 185                 190

Asn Trp Val Gln Glu Lys Pro Asp His Leu Phe Thr Gly Leu Ile Gly
            195                 200                 205

Gly Thr Asn Asn Arg Ala Pro Gly Val Pro Ala Arg Phe Ser Gly Ser
     210                 215                 220

Leu Ile Gly Asp Lys Ala Ala Leu Thr Ile Thr Gly Ala Gln Thr Glu
225                 230                 235                 240

Asp Glu Ala Ile Tyr Phe Cys Ala Leu Trp Tyr Ser Asn His Trp Val
                245                 250                 255

Phe Gly Gly Gly Thr Lys Leu Thr Val Leu Gly Leu Glu
            260                 265

(2) INFORMATION FOR SEQ ID NO: 73:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO ( v i ) ORIGINAL SOURCE:
            ( A ) ORGANISM: Mouse ( i x ) FEATURE:
            ( A ) NAME/KEY: CDS
            ( B ) LOCATION: 1..354

( x i ) SEQUENCE DESCRIPTION: SEQ ID NO: 73:

| CAG | GTT | CAG | CTG | CAG | CAG | TCT | GGA | GCT | GAG | CTG | ATG | AAG | CCT | GGG | GCC | 48 |
| Gln | Val | Gln | Leu | Gln | Gln | Ser | Gly | Ala | Glu | Leu | Met | Lys | Pro | Gly | Ala | |
| 1 | | | | 5 | | | | | 10 | | | | | 15 | | |

| TCA | GTG | AAG | ATA | TCC | TGC | AAG | GCT | ACT | GGC | TAC | ACA | TTC | AGT | GCC | TAC | 96 |
| Ser | Val | Lys | Ile | Ser | Cys | Lys | Ala | Thr | Gly | Tyr | Thr | Phe | Ser | Ala | Tyr | |
| | | | 20 | | | | | 25 | | | | | 30 | | | |

| TGG | ATA | GAG | TGG | GTA | AAG | CAG | AGG | CCT | GGA | CAT | GGC | CTT | GAG | TGG | ATT | 144 |
| Trp | Ile | Glu | Trp | Val | Lys | Gln | Arg | Pro | Gly | His | Gly | Leu | Glu | Trp | Ile | |
| | | 35 | | | | | 40 | | | | | 45 | | | | |

| GGA | GAG | ATT | TTA | CCT | GGA | AGT | AAT | AAT | TCT | AGA | TAC | AAT | GAG | AAG | TTC | 192 |
| Gly | Glu | Ile | Leu | Pro | Gly | Ser | Asn | Asn | Ser | Arg | Tyr | Asn | Glu | Lys | Phe | |
| 50 | | | | | 55 | | | | | 60 | | | | | | |

| AAG | GGC | AAG | GCC | ACA | TTC | ACT | GCT | GAT | ACA | TCC | TCC | AAC | ACA | GCC | TAC | 240 |
| Lys | Gly | Lys | Ala | Thr | Phe | Thr | Ala | Asp | Thr | Ser | Ser | Asn | Thr | Ala | Tyr | |
| 65 | | | | | 70 | | | | | 75 | | | | | 80 | |

| ATG | CAA | CTC | AGC | AGC | CTG | ACA | TCT | GAG | GAC | TCT | GCC | GTC | TAT | TAC | TGT | 288 |
| Met | Gln | Leu | Ser | Ser | Leu | Thr | Ser | Glu | Asp | Ser | Ala | Val | Tyr | Tyr | Cys | |
| | | | | 85 | | | | | 90 | | | | | 95 | | |

| TCA | AGG | TCC | TAC | GAC | TTT | GCC | TGG | TTT | GCT | TAC | TGG | GGC | CAA | GGG | ACT | 336 |
| Ser | Arg | Ser | Tyr | Asp | Phe | Ala | Trp | Phe | Ala | Tyr | Trp | Gly | Gln | Gly | Thr | |
| | | | 100 | | | | | 105 | | | | | 110 | | | |

| CCG | GTC | ACT | GTC | TCT | GCA | | | | | | | | | | | 354 |
| Pro | Val | Thr | Val | Ser | Ala | | | | | | | | | | | |
| | | 115 | | | | | | | | | | | | | | |

( 2 ) INFORMATION FOR SEQ ID NO: 74:

( i ) SEQUENCE CHARACTERISTICS:
                ( A ) LENGTH: 118 amino acids
                ( B ) TYPE: amino acid
                ( D ) TOPOLOGY: linear ( i i ) MOLECULE TYPE: protein ( x i ) SEQUENCE DESCRIPTION: SEQ ID NO: 74:

| Gln | Val | Gln | Leu | Gln | Gln | Ser | Gly | Ala | Glu | Leu | Met | Lys | Pro | Gly | Ala |
| 1 | | | | 5 | | | | | 10 | | | | | 15 | |

| Ser | Val | Lys | Ile | Ser | Cys | Lys | Ala | Thr | Gly | Tyr | Thr | Phe | Ser | Ala | Tyr |
| | | | 20 | | | | | 25 | | | | | 30 | | |

| Trp | Ile | Glu | Trp | Val | Lys | Gln | Arg | Pro | Gly | His | Gly | Leu | Glu | Trp | Ile |
| | | 35 | | | | | 40 | | | | | 45 | | | |

| Gly | Glu | Ile | Leu | Pro | Gly | Ser | Asn | Asn | Ser | Arg | Tyr | Asn | Glu | Lys | Phe |
| | 50 | | | | | 55 | | | | | 60 | | | | |

| Lys | Gly | Lys | Ala | Thr | Phe | Thr | Ala | Asp | Thr | Ser | Ser | Asn | Thr | Ala | Tyr |
| 65 | | | | | 70 | | | | | 75 | | | | | 80 |

| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |

| Ser | Arg | Ser | Tyr | Asp | Phe | Ala | Trp | Phe | Ala | Tyr | Trp | Gly | Gln | Gly | Thr |
| | | | 100 | | | | | 105 | | | | | 110 | | |

| Pro | Val | Thr | Val | Ser | Ala |
| | | 115 | | | |

( 2 ) INFORMATION FOR SEQ ID NO: 75:

(i) SEQUENCE CHARACTERISTICS:
  (A) LENGTH: 342 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iii) ANTI-SENSE: NO (vi) ORIGINAL SOURCE:
  (A) ORGANISM: Mouse (ix) FEATURE:
  (A) NAME/KEY: CDS
  (B) LOCATION: 1..342

(xi) SEQUENCE DESCRIPTION: SEQ ID NO: 75:

| GAC | ATT | GTG | ATG | TCA | CAG | TCT | CCA | TCC | TCC | CTA | GCT | GTG | TCA | GTT | GGA | 48 |
|---|---|---|---|---|---|---|---|---|---|---|---|---|---|---|---|---|
| Asp | Ile | Val | Met | Ser | Gln | Ser | Pro | Ser | Ser | Leu | Ala | Val | Ser | Val | Gly | |
| 1 | | | | 5 | | | | | 10 | | | | | 15 | | |

| GAG | AAG | GTT | ACT | ATG | AGC | TGC | AAG | TCC | AGT | CAG | AGC | CTT | TTA | TAT | AGT | 96 |
|---|---|---|---|---|---|---|---|---|---|---|---|---|---|---|---|---|
| Glu | Lys | Val | Thr | Met | Ser | Cys | Lys | Ser | Ser | Gln | Ser | Leu | Leu | Tyr | Ser | |
| | | | 20 | | | | | 25 | | | | | 30 | | | |

| AGC | AAT | CAA | AAG | ATC | TAC | TTG | GCC | TGG | TAC | CAG | CAG | AAA | CCA | GGG | CAG | 144 |
|---|---|---|---|---|---|---|---|---|---|---|---|---|---|---|---|---|
| Ser | Asn | Gln | Lys | Ile | Tyr | Leu | Ala | Trp | Tyr | Gln | Gln | Lys | Pro | Gly | Gln | |
| | | 35 | | | | | 40 | | | | | 45 | | | | |

| TCT | CCT | AAA | CTG | CTG | ATT | TAC | TGG | GCA | TCC | ACT | AGG | GAA | TCT | GGG | GTC | 192 |
|---|---|---|---|---|---|---|---|---|---|---|---|---|---|---|---|---|
| Ser | Pro | Lys | Leu | Leu | Ile | Tyr | Trp | Ala | Ser | Thr | Arg | Glu | Ser | Gly | Val | |
| | 50 | | | | | 55 | | | | | 60 | | | | | |

| CCT | GAT | CGC | TTC | ACA | GGC | GGT | GGA | TCT | GGG | ACA | GAT | TTC | ACT | CTC | ACC | 240 |
|---|---|---|---|---|---|---|---|---|---|---|---|---|---|---|---|---|
| Pro | Asp | Arg | Phe | Thr | Gly | Gly | Gly | Ser | Gly | Thr | Asp | Phe | Thr | Leu | Thr | |
| 65 | | | | | 70 | | | | | 75 | | | | | 80 | |

| ATC | AGC | AGT | GTG | AAG | GCT | GAA | GAC | CTG | GCA | GTT | TAT | TAC | TGT | CAG | CAA | 288 |
|---|---|---|---|---|---|---|---|---|---|---|---|---|---|---|---|---|
| Ile | Ser | Ser | Val | Lys | Ala | Glu | Asp | Leu | Ala | Val | Tyr | Tyr | Cys | Gln | Gln | |
| | | | | 85 | | | | | 90 | | | | | 95 | | |

| TAT | TAT | AGA | TAT | CCT | CGG | ACG | TTC | GGT | GGA | GGC | ACC | AAG | CTG | GAA | ATC | 336 |
|---|---|---|---|---|---|---|---|---|---|---|---|---|---|---|---|---|
| Tyr | Tyr | Arg | Tyr | Pro | Arg | Thr | Phe | Gly | Gly | Gly | Thr | Lys | Leu | Glu | Ile | |
| | | | 100 | | | | | 105 | | | | | 110 | | | |

| AAA | CGG | | | | | | | | | | | | | | | 342 |
|---|---|---|---|---|---|---|---|---|---|---|---|---|---|---|---|---|
| Lys | Arg | | | | | | | | | | | | | | | |

(2) INFORMATION FOR SEQ ID NO: 76:

(i) SEQUENCE CHARACTERISTICS:
  (A) LENGTH: 114 amino acids
  (B) TYPE: amino acid
  (D) TOPOLOGY: linear (ii) MOLECULE TYPE: protein (xi) SEQUENCE DESCRIPTION: SEQ ID NO: 76:

| Asp | Ile | Val | Met | Ser | Gln | Ser | Pro | Ser | Ser | Leu | Ala | Val | Ser | Val | Gly |
|---|---|---|---|---|---|---|---|---|---|---|---|---|---|---|---|
| 1 | | | | 5 | | | | | 10 | | | | | 15 | |

| Glu | Lys | Val | Thr | Met | Ser | Cys | Lys | Ser | Ser | Gln | Ser | Leu | Leu | Tyr | Ser |
|---|---|---|---|---|---|---|---|---|---|---|---|---|---|---|---|
| | | | 20 | | | | | 25 | | | | | 30 | | |

| Ser | Asn | Gln | Lys | Ile | Tyr | Leu | Ala | Trp | Tyr | Gln | Gln | Lys | Pro | Gly | Gln |
|---|---|---|---|---|---|---|---|---|---|---|---|---|---|---|---|
| | | 35 | | | | | 40 | | | | | 45 | | | |

| Ser | Pro | Lys | Leu | Leu | Ile | Tyr | Trp | Ala | Ser | Thr | Arg | Glu | Ser | Gly | Val |
|---|---|---|---|---|---|---|---|---|---|---|---|---|---|---|---|
| | 50 | | | | | 55 | | | | | 60 | | | | |

| Pro | Asp | Arg | Phe | Thr | Gly | Gly | Gly | Ser | Gly | Thr | Asp | Phe | Thr | Leu | Thr |
|---|---|---|---|---|---|---|---|---|---|---|---|---|---|---|---|
| 65 | | | | | 70 | | | | | 75 | | | | | 80 |

| Ile | Ser | Ser | Val | Lys | Ala | Glu | Asp | Leu | Ala | Val | Tyr | Tyr | Cys | Gln | Gln |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Tyr | Arg | Tyr | Pro | Arg | Thr | Phe | Gly | Gly | Gly | Thr | Lys | Leu | Glu | Ile |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

Lys Arg (2) INFORMATION FOR SEQ ID NO: 77:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (ix) FEATURE:
        (A) NAME/KEY: CDS
        (B) LOCATION: 1..354

(xi) SEQUENCE DESCRIPTION: SEQ ID NO: 77:

```
CAG  GTG  CAG  CTG  GTG  CAG  TCT  GGG  GCA  GAG  GTG  AAA  AAG  CCT  GGG  GCC     48
Gln  Val  Gln  Leu  Val  Gln  Ser  Gly  Ala  Glu  Val  Lys  Lys  Pro  Gly  Ala
 1                   5                   10                  15

TCA  GTG  AAG  GTG  TCC  TGC  AAG  GCT  TCT  GGC  TAC  ACC  TTC  AGT  GCC  TAC     96
Ser  Val  Lys  Val  Ser  Cys  Lys  Ala  Ser  Gly  Tyr  Thr  Phe  Ser  Ala  Tyr
             20                  25                  30

TGG  ATA  GAG  TGG  GTG  CGC  CAG  GCT  CCA  GGA  AAG  GGC  CTC  GAG  TGG  GTC    144
Trp  Ile  Glu  Trp  Val  Arg  Gln  Ala  Pro  Gly  Lys  Gly  Leu  Glu  Trp  Val
         35                  40                  45

GGA  GAG  ATT  TTA  CCT  GGA  AGT  AAT  AAT  TCT  AGA  TAC  AAT  GAG  AAG  TTC    192
Gly  Glu  Ile  Leu  Pro  Gly  Ser  Asn  Asn  Ser  Arg  Tyr  Asn  Glu  Lys  Phe
     50                  55                  60

AAG  GGC  CGA  GTG  ACA  GTC  ACT  AGA  GAC  ACA  TCC  ACA  AAC  ACA  GCC  TAC    240
Lys  Gly  Arg  Val  Thr  Val  Thr  Arg  Asp  Thr  Ser  Thr  Asn  Thr  Ala  Tyr
 65                  70                  75                  80

ATG  GAG  CTC  AGC  AGC  CTG  AGG  TCT  GAG  GAC  ACA  GCC  GTC  TAT  TAC  TGT    288
Met  Glu  Leu  Ser  Ser  Leu  Arg  Ser  Glu  Asp  Thr  Ala  Val  Tyr  Tyr  Cys
                 85                  90                  95

GCA  AGA  TCC  TAC  GAC  TTT  GCC  TGG  TTT  GCT  TAC  TGG  GGC  CAA  GGG  ACT    336
Ala  Arg  Ser  Tyr  Asp  Phe  Ala  Trp  Phe  Ala  Tyr  Trp  Gly  Gln  Gly  Thr
             100                 105                 110

CTG  GTC  ACA  GTC  TCC  TCA                                                      354
Leu  Val  Thr  Val  Ser  Ser
         115
```

(2) INFORMATION FOR SEQ ID NO: 78:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 78:

| Gln | Val | Gln | Leu | Val | Gln | Ser | Gly | Ala | Glu | Val | Lys | Lys | Pro | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Val | Ser | Cys | Lys | Ala | Ser | Gly | Tyr | Thr | Phe | Ser | Ala | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Trp | Ile | Glu | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|

```
                     3 5                           4 0                            4 5
Gly  Glu  Ile  Leu  Pro  Gly  Ser  Asn  Asn  Ser  Arg  Tyr  Asn  Glu  Lys  Phe
          50                           55                          60

Lys  Gly  Arg  Val  Thr  Val  Thr  Arg  Asp  Thr  Ser  Thr  Asn  Thr  Ala  Tyr
 65                           70                          75                          80

Met  Glu  Leu  Ser  Ser  Leu  Arg  Ser  Glu  Asp  Thr  Ala  Val  Tyr  Tyr  Cys
                    85                           90                          95

Ala  Arg  Ser  Tyr  Asp  Phe  Ala  Trp  Phe  Ala  Tyr  Trp  Gly  Gln  Gly  Thr
                   100                          105                         110

Leu  Val  Thr  Val  Ser  Ser
               115
```

( 2 ) INFORMATION FOR SEQ ID NO: 79:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 1..342

( x i ) SEQUENCE DESCRIPTION: SEQ ID NO: 79:

```
GAC  ATC  CAG  ATG  ACC  CAG  AGC  CCA  AGC  AGC  CTG  AGC  GCC  AGC  GTG  GGT         48
Asp  Ile  Gln  Met  Thr  Gln  Ser  Pro  Ser  Ser  Leu  Ser  Ala  Ser  Val  Gly
 1                    5                          10                          15

GAC  AGA  GTG  ACC  ATC  ACC  TGT  AAG  TCC  AGT  CAG  AGC  CTT  TTA  TAT  AGT         96
Asp  Arg  Val  Thr  Ile  Thr  Cys  Lys  Ser  Ser  Gln  Ser  Leu  Leu  Tyr  Ser
                     20                          25                          30

AGC  AAT  CAA  AAG  ATC  TAC  TTG  GCC  TGG  TAC  CAG  CAG  AAG  CCA  GGT  AAG        144
Ser  Asn  Gln  Lys  Ile  Tyr  Leu  Ala  Trp  Tyr  Gln  Gln  Lys  Pro  Gly  Lys
          35                           40                          45

GCT  CCA  AAG  CTG  CTG  ATC  TAC  TGG  GCA  TCC  ACT  AGG  GAA  TCT  GGT  GTG        192
Ala  Pro  Lys  Leu  Leu  Ile  Tyr  Trp  Ala  Ser  Thr  Arg  Glu  Ser  Gly  Val
     50                           55                          60

CCA  AGC  AGA  TTC  AGC  GGT  AGC  GGT  AGC  GGT  ACC  GAC  TTC  ACC  TTC  ACC        240
Pro  Ser  Arg  Phe  Ser  Gly  Ser  Gly  Ser  Gly  Thr  Asp  Phe  Thr  Phe  Thr
 65                           70                          75                          80

ATC  AGC  AGC  CTC  CAG  CCA  GAG  GAC  ATC  GCC  ACC  TAC  TAC  TGC  CAG  CAA        288
Ile  Ser  Ser  Leu  Gln  Pro  Glu  Asp  Ile  Ala  Thr  Tyr  Tyr  Cys  Gln  Gln
                    85                           90                          95

TAT  TAT  AGA  TAT  CCT  CGG  ACG  TTC  GGC  CAA  GGG  ACC  AAG  GTG  GAA  ATC        336
Tyr  Tyr  Arg  Tyr  Pro  Arg  Thr  Phe  Gly  Gln  Gly  Thr  Lys  Val  Glu  Ile
                   100                          105                         110

AAA  CGT                                                                              342
Lys  Arg
```

( 2 ) INFORMATION FOR SEQ ID NO: 80:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 80:

-continued

| Asp 1 | Ile | Gln | Met | Thr 5 | Gln | Ser | Pro | Ser | Ser 10 | Leu | Ser | Ala | Ser | Val 15 | Gly |
| --- | --- | --- | --- | --- | --- | --- | --- | --- | --- | --- | --- | --- | --- | --- | --- |
| Asp | Arg | Val | Thr 20 | Ile | Thr | Cys | Lys | Ser 25 | Ser | Gln | Ser | Leu | Leu 30 | Tyr | Ser |
| Ser | Asn | Gln 35 | Lys | Ile | Tyr | Leu | Ala 40 | Trp | Tyr | Gln | Gln | Lys 45 | Pro | Gly | Lys |
| Ala | Pro 50 | Lys | Leu | Leu | Ile | Tyr 55 | Trp | Ala | Ser | Thr | Arg 60 | Glu | Ser | Gly | Val |
| Pro 65 | Ser | Arg | Phe | Ser | Gly 70 | Ser | Gly | Ser | Gly | Thr 75 | Asp | Phe | Thr | Phe | Thr 80 |
| Ile | Ser | Ser | Leu | Gln 85 | Pro | Glu | Asp | Ile | Ala 90 | Thr | Tyr | Tyr | Cys | Gln 95 | Gln |
| Tyr | Tyr | Arg | Tyr 100 | Pro | Arg | Thr | Phe | Gly 105 | Gln | Gly | Thr | Lys | Val 110 | Glu | Ile |
| Lys | Arg | | | | | | | | | | | | | | |

ADENOVIRUS WITH MODIFIED BINDING MOIETY SPECIFIC FOR THE TARGET CELLS

This Application is the national stage filing under 35 U.S.C. 371 of PCT/GB93/02267, which was filed on Nov. 4, 1993, published as WO94/10323 May 11, 1994.

The present invention relates to delivery vehicles for genes to target cells, especially in the fields of gene therapy and cancer treatment.

The delivery of genes to target cells, especially those within the mammalian body, has many uses, for example in the fields of gene therapy, cancer treatment and in areas of genetic manipulation still to be discovered. The gene to be delivered may encode a molecule, such as a protein or RNA, which is cytotoxic to the target cell, or it may encode a functional copy of a gene that is defective in the target cell. In this latter case the product of the aforementioned functional copy of the gene will replace that of the defective copy, and the target cell will be able to perform its proper function.

The use of viruses, or virus-like particles, to deliver genes for gene therapy and cancer treatment has been disclosed.

However, in most cases the targeting of the virus or virus-like particles containing the desired gene to the cell has relied on the natural host-virus specificity or on local application of the virus to the cells to be targeted, for example direct application of viruses to lung cells by inhalation.

The human adenovirus 5 (Ad5) genome consists of a double-stranded linear DNA molecule of 36 kilo-basepair. The virus replication cycle has two phases: an early phase, during which four transcriptional units E1, E2, E3, and E4 are expressed, and a late phase occurring after the onset of viral DNA synthesis when late transcripts are expressed from the major late promoter (MLP). These late messages encode most of the viral structural proteins. E1, E2, and E4 gene products of human adenoviruses (Ads) are involved in transcriptional activation, cell transformation, and viral DNA replication as well as other viral functions, and are essential for viral growth. In contrast, E3 gene products are not required for viral replication in cultured cells or for acute lung infection of cotton rats, but appear to be involved in evading immune surveillance in vivo.

By "virus-like particle" we mean a nucleoprotein particle containing a core of nucleic acid surrounded by protein which (i) is not infective and (ii) can only be propagated in a suitable cell system following transformation by its nucleic acid. Thus a virus-like particle of mammalian origin may be propagated in *Saccharomyces cerevisiae* or in insect cells via a baculovirus expression system.

The modification of coat proteins of filamentous bacteriophages (bacterial viruses), such as M13 and fd, so as to generate novel binding properties, has been disclosed in Cwirla et al (1990) *Proc. Natl. Acad. Sci. USA* 87, 6378–6382 and Scott & Smith (1990) *Science* 249, 386–390.

It has previously been suggested that retroelement particles, including retroviral vectors, may be modified to target specific cells, for example see Kingsman et al (1991) *Tibtech* 9, 303–309.

Russell et al (1993) *Nucl. Acids Res.* 21, 1081–1085, published after the priority date for this application but before the filing date discloses retroviral vectors displaying functional antibody fragments and suggests that, in principle, the display of antibody fragments on the surface of recombinant retroviral particles could be used to target virus to cells for gene delivery. However, it is not known whether a retrovirus can be assembled in which all the subunits of the viral envelope protein are fused to antibody, and if so whether the virus would infect cells. NIP-derivatised human cells were tested as a method for targeted gene delivery, but became permissive for both modified (displaying an anti-NIP antibody) and unmodified ecotropic viral particles. NIP is 4hydroxy-3-iodo-5-nitrophenylacetic acid.

Michael et al (1993) *J. Biol. Chem.* 268, 6866–6869, published after the priority date of this application but before the filing date, describes molecular conjugates between adenovirus and a vector system comprising two linked domains, a DNA binding domain and a ligand domain. In this configuration, however, it is stated that the viral moiety functions in the capacity of both an alternate ligand domain of the conjugate and, since an additional ligand has been introduced into the conjugate design, the potential for cell-specific targeting is undermined.

Curiel et al (1992) *Human Gene Therapy* 3, 147–154 describes adenoviruses wherein a foreign epitope was introduced into the hexon protein and polylysine-antibody complexed DNA was attached to adenovirus by virtue of the antibody binding the foreign epitope on the hexon. Foreign DNA is transferred bound to the exterior of the virion.

The above-mentioned viruses and virus-like particles may be able to target cells using the binding moiety displayed on their surface but they can also still target their natural host cells.

We have now devised new viruses and virus-like particles at least some of which can bind the target cell with high specificity and may deliver genetic material to the target cell; at least some of the viruses and virus-like particles may bind and deliver genetic material to the target cell without substantially binding to the natural host cell of the virus.

One aspect of the present invention provides a virus, or virus-like particle, derived from a virus or virus-like particle having a receptor for a host cell comprising a modified binding specificity conferred by a binding moiety allowing the virus or virus-like particle to bind to a target cell characterised in that the said host cell receptor is modified or absent so that the virus or virus-like particle is substantially incapable of binding the said host cell.

By "a virus or virus-like particle substantially incapable of binding its host cell" is included a modified virus has no more than 1% of the binding affinity of the unmodified virus for the host cell.

In general, the binding specificity of a natural virus or virus-like particle is conferred by the specific interaction between a receptor-like molecule expressed on the surface of the virus or virus-like particle and a cognate receptor-like molecule expressed on the surface of its host cell. The invention provides a beneficial modification of the binding specificity, so that the virus or virus-like particle can bind to a different specific target cell.

The introduction of the modified binding moiety may be such as to achieve the said removal of the native binding specificity.

A second aspect of the invention comprises an adenovirus or influenza virus or vaccinia virus, or a replication-defective derivative of any of these, characterised in that the virus has a modified binding specificity conferred by a binding moiety allowing the virus to bind to a target cell.

By "binding moiety" we mean a molecule that is exposed on the surface of the virus or virus-like particle which is able to bind to a molecule on the target cell. The "binding moiety" may be a molecule on the virus or virus-like particle modified in such a way that its binding specificity is changed, or it may be a molecule added to, and exposed on the surface of, the virus or virus-like particle to provide a new binding specificity.

It is preferred if the binding moiety is external to the receptor for its host cell of the naive, unmodified virus.

It is further preferred if the binding moiety is joined or fused to the virus or virus-like particles directly or indirectly by a spacer group.

By "host cell" we mean the cell that an unmodified, naive virus can bind to using its receptor-like molecule and the cognate receptor-like molecule on the cell. By "target cell" we mean the cell that the modified virus can bind to using its binding moiety. In some circumstances in the context of the second aspect of the invention, such as when the binding moiety recognises an entity on the host cell which is not the cognate receptor-like molecule, then the host cell may be the target cell.

The virus or virus-like particle may be a bacteriophage and the target cell a bacterium in which case the invention may find uses in the treatment of bacterial infections.

In a preferred embodiment of the invention the target cell is eukaryotic. The eukaryotic cell may be a yeast cell and the virus or virus-like particle may be useful in the medical field in treating yeast infections such as athlete's foot or Candida infection but it is preferred that the eukaryotic cell is mammalian, and it is expected that the invention will find uses in the areas of gene therapy and cancer treatment.

In preferred embodiments of the first aspect of the invention the virus or virus-like particle is adenovirus or influenza virus or a pox-virus such as vaccinia.

It is also preferred that the virus or virus-like particle is "replication-defective". By "replication defective" we mean a virus whose genetic material has been manipulated so that it cannot divide or proliferate in the cell it infects.

The binding moiety of the virus or virus-like particle of the invention provides the target cell binding specificity. Any cell-binding protein or peptide or carbohydrate or lipid may be useful for targeting the virus or virus-like particle to the cell. For example, short linear stretches of amino acids, such as those constituting a peptide hormone, are useful, as are domains of polypeptides that can fold independently into a structure that can bind to the target cell.

In one preferred embodiment the binding moiety has the property of any one of a monoclonal antibody, ScFv (single chain Fv fragment), a dAb (single domain antibody) or a minimal recognition unit of an antibody.

The binding site on the target cell may be a target cell-specific antigen. Such antigens are listed in Table 1. Other binding moieties, targets on cells, and diseases which could usefully be treated using reagents delivered by the modified viruses or virus-like particles are given in Table 2.

TABLE 1

| Antigen | Antibody | Existing Uses |
|---|---|---|
| 1. Tumour Associated Antigens | | |
| Carcino-embryonic Antigen | {C46 (Amersham) {85A12 (Unipath) | Imaging & Therapy of colon/rectum tumours. |
| Placental Alkaline Phosphatase | H17E2 (ICRF, Travers & Bodmer) | Imaging & Therapy of testicular and ovarian cancers. |
| Pan Carcinoma | NR-LU-10 (NeoRx Corporation) | Imaging & Therapy of various carcinomas incl. small cell lung cancer. |
| Polymorphic Epithelial Mucin (Human milk fat globule) | HMFG1 (Taylor Papadimitriou, ICRF) | Imaging & Therapy of ovarian cancer, pleural effusions. |
| β-human Chorionic Gonadotropin | W14 | Targeting of enzyme (CPG2) to human xenograft choriocarcinoma in nude mice. (Searle et al (1981) Br. J. Cancer 44, 137–144) |
| A Carbohydrate on Human Carcinomas | L6(IgG2a)[1] | Targeting of alkaline phosphatase (Senter et al (1988) P.N.A.S. 85, 4842–4846 |
| CD20 Antigen on B Lymphoma (normal and neoplastic) | 1F5 (IgG2a)[2] | Targeting of alkaline phosphatase. (Senter et al (1988) P.N.A.S. 85, 4842–4846 |
| Other antigens include alphafoetoprotein, Ca-125 and prostate specific antigen. | | |
| 2. Immune Cell Antigens | | |
| Pan T Lymphocyte Surface Antigen (CD3) | OKT-3 (Ortho) | As anti-rejection therapy for kidney transplants. |
| B-lymphocyte Surface Antigen (CD22) | RFB4 (Janossy, Royal Free Hospital) | Immunotoxin therapy of B cell lymphoma. |
| Pan T lymphocyte Surface Antigen (CD5) | H65 (Bodmer, Knowles ICRF, Licensed to Xoma Corp., USA) | Immunotoxin treatment of Acute Graft versus Host disease, Rheumatoid Arthritis. |
| 3. Infectious Agent-Related Antigens | | |
| Mumps virus-related | Anti-mumps polyclonal antibody | Antibody conjugated to Diphtheria toxin for treatment of mumps. |
| Hepatitis B Surface Antigen | Anti HBs Ag | Immunotoxin against Hepatoma. |

[1]Hellström et al (1986) Cancer Res. 46, 3917–3923
[2]Clarke et al (1985) P.N.A.S. 82, 1766–1770

TABLE 2

Binding moieties for tumour-specific targets and tumour associated antigens

| Target | Binding moiety | Disease |
|---|---|---|
| Truncated EGFR | anti-EGFR mAb | Gliomas |
| Idiotypes | anti-id mAbs | B-cell lymphomas |
| EGFR (c-erbB1) | EGF, TGFα anti-EGFR mAb | Breast cancer |
| c-erbB2 | mAbs | Breast cancer |
| IL-2 receptor | IL-2 anti-Tac mAb | Lymphomas and leukaemias |
| IL-4 receptor | IL-4 | Lymphomas and leukaemias |
| IL-6 receptor | IL-6 | Lymphomas and leukaemias |
| MSH (melanocyte-stimulating hormone) receptor | α-MSH | Melanomas |
| Transferrin receptor TR) | Transferrin anti-TR mAb | Gliomas |
| gp95/gp97 | mAbs | Melanomas |
| p-glycoprotein cells | mAbs | drug-resistant |
| cluster-1 antigen (N- | mAbs | Small cell lung |

TABLE 2-continued

Binding moieties for tumour-specific targets and tumour associated antigens

| Target | Binding moiety | Disease |
|---|---|---|
| CAM) | | carcinomas |
| cluster-w4 | mAbs | Small cell lung carcinomas |
| cluster-5A | mAbs | Small cell lung carcinomas |
| cluster-6 (LeY) | mAbs | Small cell lung carcinomas |
| PLAP (placental alkaline phosphatase) | mAbs | Some seminomas Some ovarian; some non-small cell lung cancer |
| CA-125 | mAbs | Lung, ovarian carcinoma |
| ESA (epithelial specific antigen) | mAbs | |
| CD 19, 22, 37 | mAbs | B-cell lymphoma |
| 250 kDa proteoglycan | mAbs | Melanoma |
| p55 | mAbs | Breast cancer |
| TCR-IgH fusion | mAbs | Childhood T-cell leukaemia |
| Blood gp A antigen (in B or O individuals) | mAbs | Gastric and colon tumours |

The binding moiety may be a monoclonal antibody. Monoclonal antibodies which will bind to many of these antigens are already known but in any case, with today's techniques in relation to monoclonal antibody technology, antibodies can be prepared to most antigens. The binding moiety may be a part of an antibody (for example a Fab fragment) or a synthetic antibody fragment (for example, ScFv). Suitable monoclonal antibodies to selected antigens may be prepared by known techniques, for example those disclosed in "*Monoclonal Antibodies: A manual of techniques*", H. Zola (CRC Press, 1988) and in "*Monoclonal Hybridoma Antibodies: Techniques and Applications*", J. G. R. Hurrell (CRC Press, 1982).

Suitably prepared non-human antibodies can be "humanized" in known ways, for example by inserting the CDR regions of mouse antibodies into the framework of human antibodies.

The variable heavy ($V_H$) and variable light ($V_L$) domains of the antibody are involved in antigen recognition, a fact first recognised by early protease digestion experiments. Further confirmation was found by "humanization" of rodent antibodies. Variable domains of rodent origin may be fused to constant domains of human origin such that the resultant antibody retains the antigenic specificity of the rodent parental antibody (Morrison et al (1984) *Proc. Natl. Acad. Sci. USA* 81, 6851–6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); ScFv molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and dAbs comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293–299.

By "ScFv molecules" we mean molecules wherein the $V_H$ and $V_L$ partner domains are linked via a flexible oligopeptide.

It may be advantageous to use antibody fragments, rather than whole antibodies. Effector functions of whole antibodies, such as complement binding, are removed. ScFv and dAb antibody fragments can be expressed as fusions with other polypeptides.

Minimal recognition units may be derived from the sequence of one or more of the complementary-determining regions (CDR) of the Fv fragment. Whole antibodies, and F(ab')$_2$ fragments are "bivalent". By "bivalent" we mean that the said antibodies and F(ab')$_2$ fragments have two antigen combining sites. In contrast, Fab, Fv, ScFv, dAb fragments and minimal recognition units are monovalent, having only one antigen combining sites.

In a further embodiment the binding moiety is at least part of a ligand of a target cell-specific cell-surface receptor.

It is preferred that the target cell-specific cell-surface receptor is the receptor for human gonadotrophin releasing hormone (GnRH). In this preferred embodiment the binding moiety is GnRH, and its binding specificity is for human cancer cells that express the GnRH receptors on their surface. Examples of such human cancer cells are prostate, breast and endometrial cancer cells.

It is also preferred that the target cell-specific cell-surface receptor is the receptor for melanocyte-stimulating hormone (MSH) which is expressed in high number in melanoma cells. In this preferred embodiment the binding moiety is MSH, and its binding specificity is for melanoma cells.

It is also preferred that the target cell-specific cell-surface receptor is the receptor for somatostatin.

Of course, the receptors for GnRH, MSH and somatostatin may themselves be target cell-specific antigens and may be recognised by binding moieties which have the property of any one of a monoclonal antibody, a ScFv, a dAb or a minimal recognition unit. Thus, although the binding site on the target cell may be a cell-surface receptor it may also act as a target cell-specific cell-surface antigen for recognition by the binding moiety.

It will be appreciated by those skilled in the art that binding moieties which are polypeptides may be conveniently made using recombinant DNA techniques. The binding moiety may be fused to a protein on the surface of the virus or virus-like protein as disclosed below or they may be synthesised independently of the virus or virus-like particle, by expression from a suitable vector in a suitable host and then joined to the virus or virus-like particle as disclosed below.

Nucleic acid sequences encoding many of the targeting moieties are known, for example those for peptide hormones, growth factors, cytokines and the like and may readily be found by reference to publicly accessible nucleotide sequence databases such as EMBL and GenBank. Once the nucleotide sequence is known it is obvious to the person skilled in the art how to make DNA encoding the chosen binding moiety using, for example, chemical DNA synthetic techniques or by using the polymerase chain reaction to amplify the required DNA from genomic DNA or from tissue-specific cDNA.

Many cDNAs encoding peptide hormones, growth factors, cytokines and the like, all of which may be useful as binding moieties, are generally available from, for example British Biotechnology Ltd, Oxford, UK.

It is preferred that when the virus or virus-like particle of the invention binds to its target cell it delivers its nucleic acid to the said target cell, that is the target cell is infected by the virus or virus-like particle. Target cells, especially cancer cells, that are infected in this manner by the virus or virus-like particle may express viral molecules on their surface and may be recognised by the immune system and destroyed. Of course, other cytotoxic functions of the virus may also kill the cell.

In one embodiment when the virus or virus-like particle is adenovirus, the E1B gene is substantially deleted or modified so that its gene product no longer interacts with the E1A protein. E1A protein stimulates apoptosis but normally its action is inhibited by E1B. Conveniently, the E1B gene is inactivated by insertion; preferably a cytotoxic gene, as defined below, is inserted at or near the E1B gene.

E1, E3 and a site upstream of E4 may be used as sites for insertion of foreign DNA sequences in the generation of recombinant adenoviruses for example see Berkner and Sharp (1984) *Nucl. Acids Res.* 12, 1925–1941; Chanda et al (1990) *Virology* 175, 535–547; Haj-Ahmad and Graham (1986) *J. Virol.* 57, 267–274; Saito et al (1985) *J. Virol.* 54, 711–719; all incorporated herein by reference. Since the upper size limit for DNA molecules that can be packaged into adenovirus particles is approximately 105% of the wild-type genome only about 2 kb of extra DNA can be inserted without compensating deletions of viral DNA. Although E1 is essential for virus replication in cell culture, foreign DNA can be substituted for E1 sequences when the virus is grown in 293 cells which are transformed by Ad5 DNA and constitutively express E1 (Graham et al (1977) *J. Gen. Virol.* 36, 59–72, incorporated herein by reference). Several vectors having 1.9 kb deleted from E3 of Ad5 have been constructed without interfering with virus replication in cell culture (reviewed by Graham and Prevec (1992) in "Vaccines: New Approaches to Immunological Problems" R. W. Ellis (Ed.), Butterworth-Heinemann, Boston, Mass., pages 364–390, incorporated herein by reference). Such vectors allow for insertion of up to 4 kb of foreign DNA. Recombinant adenoviruses containing inserts in E3 replicate in all Ad-permissive cell lines and a number of adenovirus vectors containing E3 inserts have been shown to express foreign genes efficiently both in vitro and in vivo (Berkner (1988) *Biotechniques* 6, 616–629; Chanda et al (1990) *Virology* 175, 535–547; Dewar et al (1989) J. Virol. 63, 129–136; Graham (1990) *Trends Biotechnol.* 8, 85–87; Graham and Prevec (1992) in "Vaccines: New Approaches to Immunological Problems" R. W. Ellis (Ed.), Butterworth-Heinemann, Boston, Mass., pages 364–390; Johnson et al (1988) *Virology* 164, 1–14; Lubeck et al (1989) *Proc. Natl. Acad. Sci. USA* 86, 6763–6767; McDermott et al (1989) *Virology* 169, 244–247; Morin et al (1987) *Proc. Natl. Acad. Sci. USA* 84, 4626–4630; Prevec et al (1989) *J. Gen. Virol.* 70, 429–434; Prevec et al (1990) *J. Inf. Dis.* 161, 27–30; Schneider et al (1989) *J. Gen. Virol.* 70, 417–427; Vernon et al (1991) *J. Gen. Virol.* 72, 1243–1251; Yuasa et al (1991) *J. Gen. Virol.* 72, 1927–1934) all incorporated herein by reference.

Substantially replication-defective adenoviruses may be made by creating a deficiency of the E1A protein. Suitably this is achieved by deleting the E1A gene or by making mutations within the E1A gene that prevent expression of the E1A protein. Examples of suitable mutations are deletions within the E1A coding region; nonsense mutations; and frameshift mutations.

In further preference, the virus or virus-like particle is modified further to contain a gene suitable for gene therapy.

In one embodiment, the gene encodes a molecule having a directly or indirectly cytotoxic function. By "directly or indirectly" cytotoxic, we mean that the molecule encoded by the gene may itself be toxic (for example ricin; tumour necrosis factor; interleukin-2; interferon-gamma; ribonuclease; deoxyribonuclease; Pseudomonas exotoxin A) or it may be metabolised to form a toxic product, or it may act on something else to form a toxic product. The sequence of ricin cDNA is disclosed in Lamb et al (1985) *Eur. J. Biochem.* 148, 265–270 incorporated herein by reference.

For example, it would be desirable to target a DNA sequence encoding an enzyme using the virus or virus-like particle of the invention, the enzyme being one that converts a relatively non-toxic prodrug to a toxic drug. The enzyme cytosine deaminase converts 5-fluorocytosine (5FC) to 5-fluorouracil (5FU) (Mullen et al (1922) *PNAS* 89, 33); the herpes simplex enzyme thymidine kinase sensitises cells to treatment with the antiviral agent ganciclovir (GCV) or aciclovir (Moolten (1986) *Cancer Res.* 46, 5276; Ezzedine et al (1991) *New Biol* 3, 608). The cytosine deaminase of any organism, for example *E. coli* or *Saccharomyces cerevisiae*, may be used.

Thus, in a preferred embodiment of the invention, the gene encodes a cytosine deaminase and the patient is concomitantly given 5FC. By "concomitantly", we mean that the 5FC is administered at such a time, in relation to the transformation of the tumour cells, that 5FC is converted into 5FU in the target cells by the cytosine deaminase expressed from the said gene. A dosage of approximately 0.001 to 100.0 mg 5C/kg body weight/day, preferably 0.1 to 10.0 mg/kg/day is suitable.

Components, such as 5FC, which are converted from a relatively non-toxic form into a cytotoxic form by the action of an enzyme are termed "pro-drugs".

Other examples of pro-drug/enzyme combinations include those disclosed by Bagshawe et al (WO 88/07378), namely various alkylating agents and the Pseudomonas spp. CPG2 enzyme, and those disclosed by Epenetos & Rowlinson-Busza (WO 91/11201), namely cyanogenic prodrugs (for example amygdalin) and plant-derived β-glucosidases.

Enzymes that are useful in this embodiment of the invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs [see, e.g. R. J. Massey, *Nature,* 328, pp. 457–458 (1987)].

Similarly, the prodrugs of this invention include, but are not limited to, the above-listed prodrugs, e.g., phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted by the enzyme of the conjugate into the more active, cytotoxic free drug. Examples of cytotoxic drugs that can be derivatized into a prodrug form for use in this invention include, but are not limited to, etoposide, teniposide, adriamycin, daunomycin, carminomycin, aminopterin, dactinomycin, mitomycins, cis-platinum and cis-platinum analogues, bleomycins, esperamicins [see U.S. Pat. No. 4,675,187], 5-fluorouracil, melphalan and other related nitrogen mustards.

In a further embodiment the gene delivered to the target cell encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods, U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

In a still further embodiment the gene delivered to the target cell encodes an antisense RNA.

By "antisense RNA" we mean an RNA molecule which hybridises to, and interferes with the expression from a mRNA molecule encoding a protein or to another RNA molecule within the cell such as pre-mRNA or tRNA or rRNA, or hybridises to, and interferes with the expression from a gene.

Conveniently, a gene expressing an antisense RNA may be constructed by inserting a coding sequence encoding a protein adjacent a promoter in the appropriate orientation such that the RNA complementary to mRNA. Suitably, the antisense RNA blocks expression of undesirable polypeptides such as oncogenes, for example ras, bcl, src or tumour suppressor genes such as p53 and Rb.

It will be appreciated that it may be sufficient to reduce expression of the undesirable polypeptide rather than abolish the expression.

It will be further appreciated that DNA sequences suitable for expressing as antisense RNA may be readily derived from publicly accessible databases such as GenBank and EMBL.

In another embodiment of the invention, the gene replaces the function of a defective gene in the target cell.

There are several thousand inherited genetic diseases of mammals, including humans, that are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene.

Many types of cancer are caused by defective genes, especially protooncogenes, and tumour-suppressor genes that have undergone mutation.

Thus, it is preferred that the virus or virus-like particle of the invention, which may be useful in the treatment of cystic fibrosis, contains a functional CFTR gene to replace the function of the defective CFTR gene. Similarly, it is preferred that the virus or virus-like particle of the invention, which may be useful in the treatment of cancer, contains a functional protooncogene, or tumour-suppressor gene to replace the function of the defective protooncogene or tumour-suppressor gene.

Examples of protooncogenes are ras, src, bcl and so on; examples of tumour-suppressor genes are p53 and Rb.

By "gene" we mean a nucleic acid coding sequence that may contain introns, or fragment thereof, or cDNA, or fragment thereof.

It will be appreciated that the gene will be introduced into a convenient place within the genome of the virus or virus-like particle and will contain a promoter and/or enhancer element to drive its expression.

It is preferred if the promoter and/or enhancer is selective for the cells to be targeted. Some examples of tissue or tumour specific promoters are given below but new ones are being discovered all of the time which will be useful in this embodiment of the invention.

The tyrosinase and TRP-1 genes both encode proteins which play key roles in the synthesis of the pigment melanin, a specific product of melanocytic cells. The 5' ends of the tyrosinase and tyrosinase-related protein (TRP-1) genes confer tissue specificity of expression on genes cloned downstream of these promoter elements.

The 5' sequences of these genes are described in Bradl, M. et al (1991) *Proc. Natl. Acad. Sci. USA* 88, 164–168 and Jackson, I. J. et al (1991) *Nucleic Acids Res.* 19, 3799–3804.

Prostate-specific antigen (PSA) is one of the major protein constituents of the human prostate secretion. It has become a useful marker for the detection and monitoring of prostate cancer. The gene encoding PSA and its promoter region which directs the prostate-specific expression of PSA have been described (Lundwall (1989) *Biochem. Biophys. Res. Comm.* 161, 1151–1159; Riegman et al (1989) *Biochem. Biophys. Res. Comm.* 159, 95–102; Brawer (1991) *Acta Oncol.* 30, 161–168).

Carcinoembryonic antigen (CEA) is a widely used tumour marker, especially in the surveillance of colonic cancer patients. Although CEA is also present in some normal tissues, it is apparently expressed at higher levels in tumorous tissues than in corresponding normal tissues. The complete gene encoding CEA has been cloned and its promoter region analysed. A CEA gene promoter construct, containing approximately 400 nucleotides upstream from the translational start, showed nine times higher activity in the adenocarcinoma cell line SW303, compared with the HeLa cell line. This indicates that cis-acting sequences which convey cell type specific expression are contained within this region (Schrewe et al (1990) *Mol. Cell. Biol.* 10, 2738–2748).

The c-erbB-2 gene and promoter have been characterised previously and the gene product has been shown to be over-expressed in tumour cell lines (Kraus et al (1987) *EMBO J.* 6, 605–610).

The mucin gene, MUC1, contains 5' flanking sequences which are able to direct expression selectively in breast and pancreatic cell lines, but not in non-epithelial cell lines as taught in WO 91/09867.

The binding moiety allowing the virus or virus-like particle to bind to a target cell may be a polypeptide or oligosaccharide or lipid or any other molecule capable of binding specifically to the target cell.

It is preferred that the binding moiety is a polypeptide.

The molecule on the surface of the virus or virus-like particle to which the binding moiety is joined may be a polypeptide, oligosaccharide or lipid or any other molecule in the virus or virus-like particle coat. It is preferred that the molecule is a polypeptide.

If the binding moiety and the molecule on the surface of the virus or virus-like particle are both polypeptides then they may be linked together by any of the conventional ways of cross-linking polypeptides, such as those generally described in O'Sullivan et al *Anal. Biochem.* (1979) 100, 100–108. For example, the binding moiety may be enriched with thiol groups and the molecule on the surface of the virus or virus-like particle reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Other chemical procedures may be useful in joining oligosaccharide and lipids to other oligosaccharides, lipids or polypeptides.

It is preferred that the binding moiety and the molecule on the surface of the virus or virus-like particle are both polypeptides that may be produced as a fusion by the techniques of genetic engineering. The use of genetic engineering allows for the precise control over the fusion of such polypeptides.

Thus a further embodiment of the invention is a nucleotide sequence encoding the fusion of the binding moiety and the protein on the surface of the virus or virus-like particle.

The nucleotide sequence encoding the fusion of the binding moiety and the protein on the surface of the virus or virus-like particle is preferably made by an alteration of the viral genome.

The nucleotide sequence may be synthesised de novo using solid phase phosphoramidite chemistry, but it is more usual for the nucleotide sequence to be constructed from two parts, the first encoding the binding moiety and the second the protein on the surface of the virus or virus-like particle. The two parts may be derived from their respective genes by restriction endonuclease digestion or by other methods known by those skilled in the art such as the polymerase chain reaction.

A variety of methods have been developed to operatively link two nucleotide sequences via complementary cohesive termini. For instance, synthetic linkers containing one or more restriction sites provide a method of joining the two DNA segment together. Each DNA segment, generated by endonuclease restriction digestion, is treated with bacteriophage T4 DNA polymerase of *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments arc then cleaved with the appropriate restriction enzyme and lifted to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to generate the DNA encoding the fusion polypeptide of the invention is to use the polymerase chain reaction as disclosed by Saiki et al (1988) *Science* 239, 487–491.

In this method each of the DNA molecules encoding the two polypeptides to be fused are enzymatically amplified using two specific oligonucleotide primers which themselves become incorporated into the amplified DNA. The said specific primers may contain restriction endonuclease recognition sites which may then be used to join the said two DNA molecules using T4 DNA ligase as disclosed.

A particular feature of one aspect of the present invention is the modification of the virus or virus-like particle of the invention so that it no longer binds its host cell and so that it binds the target cell by virtue of its binding moiety.

The host-cell receptor of adenovirus may be the penton fibre and that of influenza virus may be the haemagglutinin receptor.

These receptors may be modified by the insertion or deletion or substitution of amino acid residues that disrupt their host-cell binding function. It is preferred that the binding moiety for the target cell is joined to the host-cell receptor in such a manner that the binding moiety is capable of binding the target cell, the host-cell receptor is unable to bind to the host cell and therefore the binding specificity of the virus or virus-like particle is modified. A further preference is that the portion of the host-cell receptor that is exposed on the surface of the virus or virus-like particle is replaced by the binding moiety, and that the portion of the host-cell receptor which promotes the uptake of viral DNA by the target cell is retained. Suitably, the binding moiety is joined directly or indirectly to the host-cell receptor by a spacer group.

Examples of spacer groups are polypeptide sequences of between 4 and 1000 amino acid residues.

Thus, in one embodiment of the invention the gene encoding the penton fibre in adenovirus is modified in such a way that the DNA encoding the surface-exposed portion is replaced by a DNA fragment encoding a ScFv, the ScFv being derived from an antibody which binds to a target cell surface antigen.

Potential fusion sites within the penton fibre have been identified.

The adenovirus fibre is a trimer composed of three protomers. The amino terminal end (40 amino acids or so) of each participates in the formation of a tail that is closely associated with the penton (as opposed to the hexon) subunit of the capsid. High amino acid conservation is maintained between the different characterised serotypes.

Middle portions of each protomer form the shaft of the protein. This shaft is of variable length, depending upon serotype, and is composed of repeating units of 15 amino acids (for examples, serotypes have been identified with 6, 15 and 21 repeat units). These repeating units are not duplicates: rather than strict conservation of amino acid structure, there is a general conservation of relative hydrophobicity. Some serotypes, for example, 40 and 41, have shafts composed of different length fibre proteins. This suggests a certain flexibility in structural constraints.

The carboxy-terminal ends (some 200 amino acids) associate to form a knob that is held erect a great distance (in molecular terms) from the capsid.

Whilst the cellular receptor(s) and mechanisms of docking have not been firmly identified and elucidated, we propose that the most likely candidate structure for cell binding is the knob. Thus, in one embodiment the whole knob of the penton fibre has been replaced with single chain antibody (ScFv) domains. The triplex structure implies that each fibre will thus end in three ScFvs. Additionally, the ScFv regions can be replaced with CDRs, or by non-antibody derived peptides, of known specificity or other molecules that are capable of interacting specifically with the target cell.

Suitable fusion sites are therefore at the native junction between shaft and knob domains, or (should the DNA sequence prove to be more amenable) at any junction between repetitive units of the shaft. Preferably, the minimum shaft length is not reduced beyond the smallest size naturally identified. There are thus at least 15 potential sites at which fusion could be contemplated.

Although it is preferred that the binding moiety forms the end of the fibre thereby replacing the knob, the binding moiety may also be fused within the penton fibre sequence but still display its binding surfaces and bind to the target cell.

Suitably, the binding moiety may be fused to the knob and extend externally to the knob structure.

In a further embodiment influenza virus haemmaglutinin is modified to incorporate a binding moiety. Influenza virus has seven or eight (depending on serotype) genetic segments, all negative strand RNA. Suitably, a cDNA from the whole segment encoding haemmagglutinin is constructed and modified by adding a promoter firing backwards across this segment so that negative strand RNA is made. Genetic fusions with a suitable binding molecule, as disclosed above, are made using standard recombinant DNA methods and a suitable cell line is stably transfected with this gene construct. Infection of this transfected cell line with influenza virus and selection of reassorted genomes containing the new haemmagglutinin by infection of a normally resistant cell line that expresses a marker that can only be recognised by the new haemmagglutinin yields the desired virus comprising modified cell-binding specificity.

A further aspect of the invention provides a method of producing in cell culture a virus or virus-like particle and then joining the binding moiety, as defined above, to the virus or virus-like particle.

A further aspect of the invention provides a method of producing in cell culture a virus or virus-like particle which has been genetically modified to express a binding moiety on its surface. The virus or virus-like particle is grown in its host prior to modification, but once the modification that alters the binding specificity is made, the virus or virus-like particle is grown in the target cell. Thus, for example in the case where the binding moiety recognises a breast tumour cell antigen, the virus or virus-like particle is grown in breast tumour cell culture.

The virus or virus-like particles of the invention are administered in any suitable way, usually parenterally, for example intravenously, intraperitoneally or intravesically, in standard sterile, non-pyrogenic formulations of diluents and carriers, for example isotonic saline (when administered intravenously).

A further aspect of the invention provides a method of delivery of the virus or virus-like particle which contains a gene encoding a molecule having an indirectly cytotoxic function.

Suitably, the indirectly cytotoxic function is an enzyme that converts a prodrug to a toxic drug. With such a virus or virus-like particle, once the virus or virus-like particle has bound to the target cells, delivered its nucleic acid to the cells, and expressed the indirectly cytotoxic functions, which typically takes a day or so, the pro-drug is administered. The timing between administration of the virus or virus-like particle and the pro-drug may be optimised in a non-inventive way.

The dosage of the pro-drug will be chosen by the physician according to the usual criteria. The dosage of the virus or virus-like particle will similarly be chosen according to normal criteria, and in the case of tumour treatment, particularly with reference to the type, stage and location of tumour and the weight of the patient. The duration of treatment will depend in part upon the rapidity and extent of any immune reaction to the virus or virus-like particle.

Some of the viruses or virus-like particles either in themselves, or together with an appropriate pro-drug, are in principle suitable for the destruction of cells in any tumour or other defined class of cells selectively exhibiting a recognisable (surface) entity. Examples of types of cancer that may be treated using the viruses or virus-like particles are cancer of the breast, prostate, colon, rectum, ovary, testicle and brain. The compounds are principally intended for human use but could be used for treating other mammals including dogs, cats, cattle, horses, pigs and sheep.

The invention will now be described in detail with reference to the following Figures and Examples in which:

FIG. 1(a)–(c) shows (a) an unmodified (i.e. "naive") virus or virus-like particle able to bind to and infect its host cell but not a non-host cell, such as a target cell; and (b) a virus or virus-like particle with a modified binding specificity does not bind and infect its host cell but binds and infects a target cell; and (c) a virus or virus-like particle as in (b) modified further to contain a gene for gene therapy or cancer treatment.

FIG. 2(a)–(c) shows (a) unmodified (naive) adenovirus; (b) adenovirus modified so that its penton fibres, which recognise the host cell, are replaced in part by antibody fragments which recognise the target cell; and (c) adenovirus as in (b) with further genetic material added to the viral DNA for gene therapy of cancer.

FIG. 3(a)–(b) shows (a) influenza virus and (b) genetically-modified influenza virus wherein at least part of the haemagglutinin binding site is replaced by an antibody with anti-cancer cell binding activity.

FIG. 4(a)–(b) shows (a) a retrovirus virus; and (b) as in (a) except the retrovirus has been modified further to express on its surface an anticancer cell-binding antibody fragment or an anticancer cell-binding peptide.

FIG. 6 shows fusions between the DNA encoding the Ad5 fibre and an ScFv (SEQ. ID NO. 1 through 43, as depicted in the Key to Sequence Listing set forth hereinafter.

FIG. 7 shows sequences of oligonucleotides used for amplifying the ScFv. All oligonucleotides are presented 5' to 3', the reverse complement of FOR primers are shown and derived amino acid sequences are shown where relevant. (SEQ. ID NO. 46 and 47, as depicted in the Key to Sequence Listing set forth hereinafter).

Figure 1A:
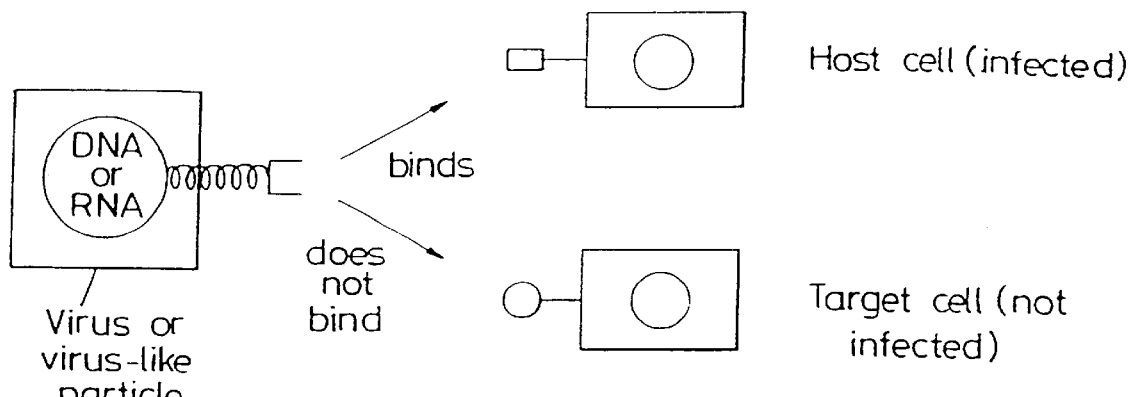
Figure 1B:
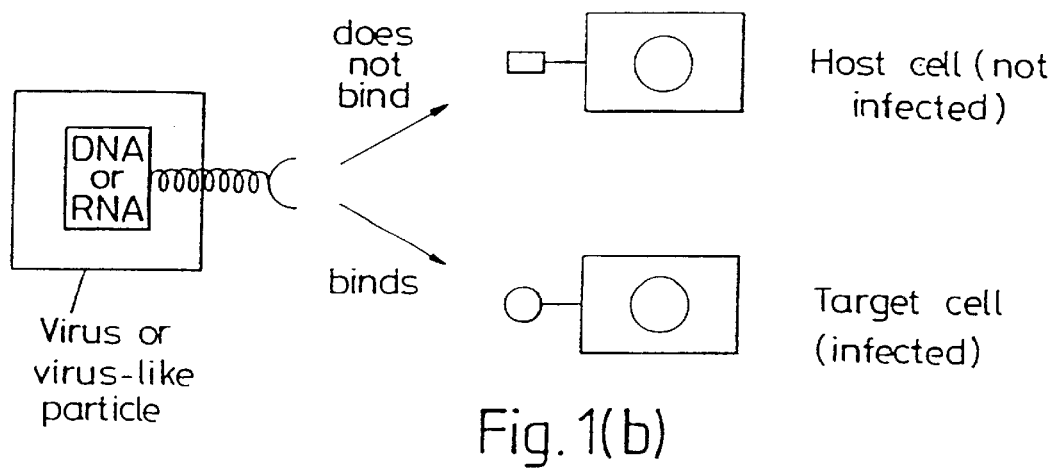
Figure 1C:
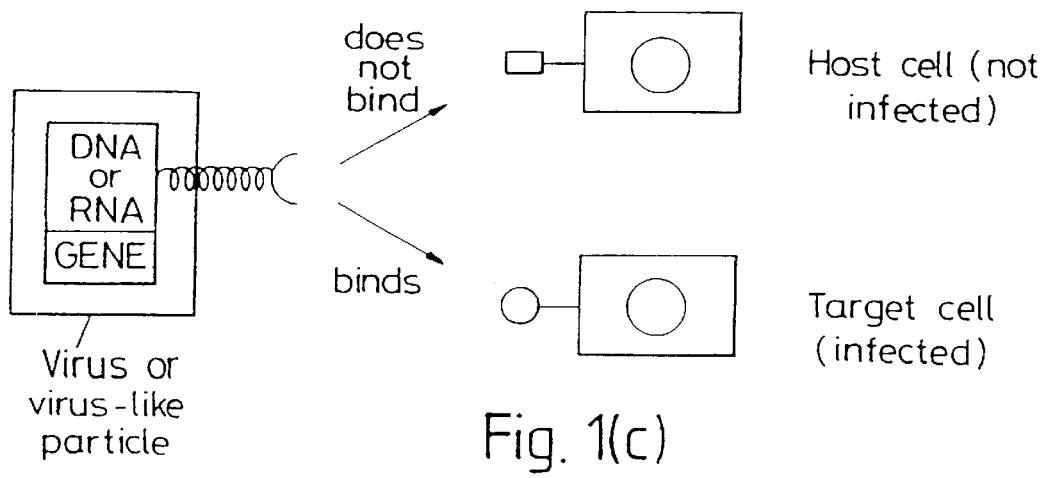
Figure 2A:
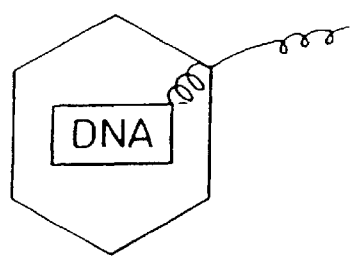
Figure 2B:
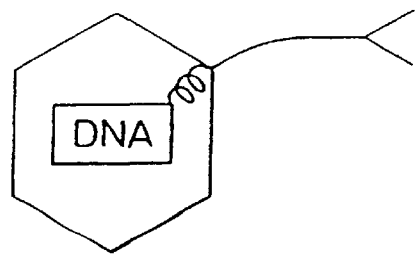
Figure 2C:
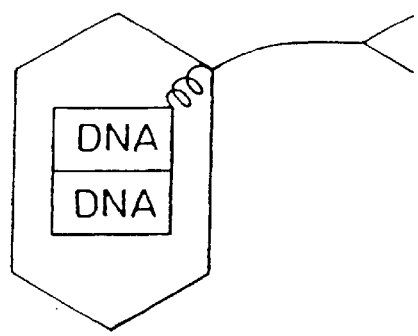
Figure 3A:
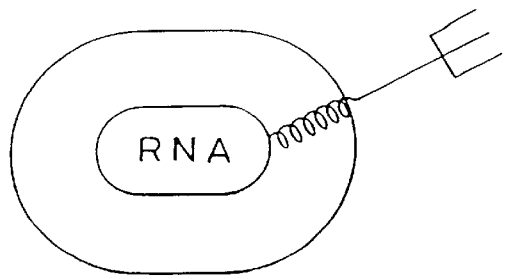
Figure 3B:
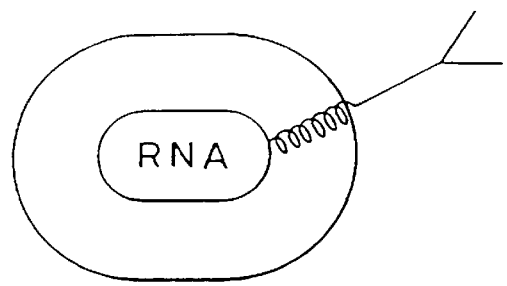
Figure 4A:
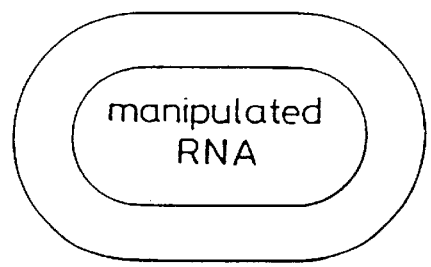
Figure 4B:
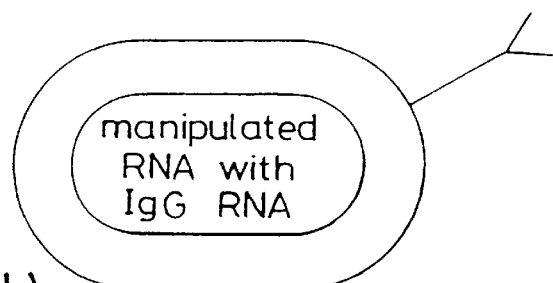
Figure 5:
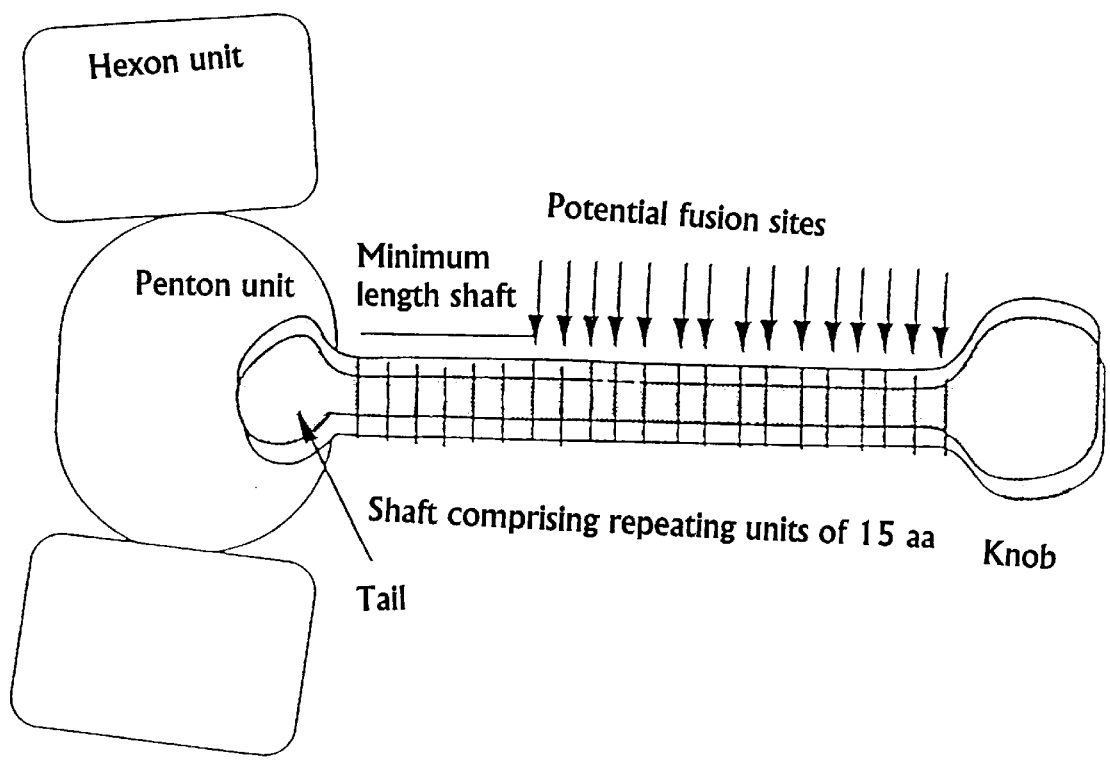
FIG. 5 is a diagrammatic representation of a penton fibre indicating potential fusion sites within the fibre.
Figure 8:
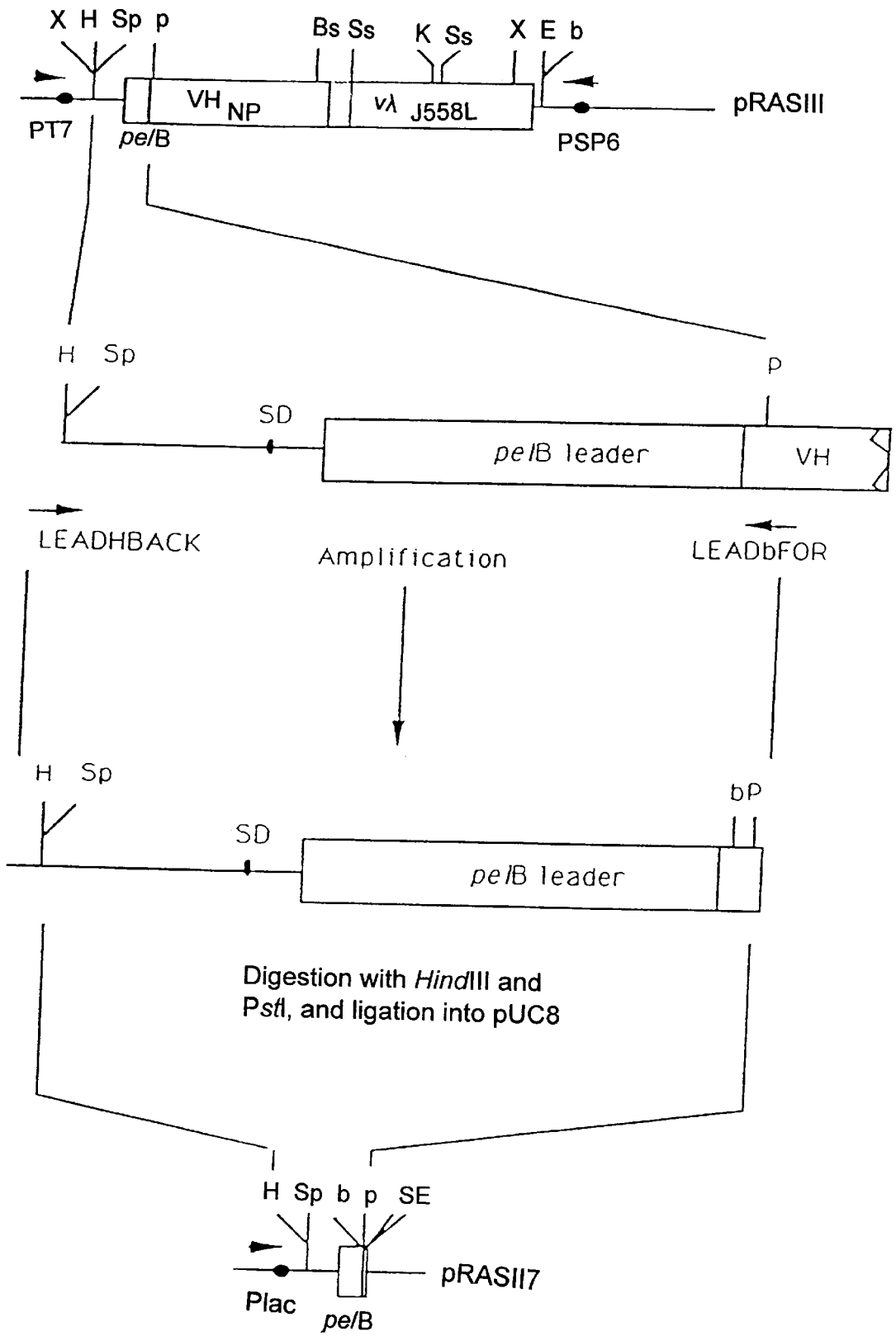

FIG. 8 shows the construction of plasmid pRAS117.

FIG. 9 shows the nucleotide and derived amino acid sequence between the HindIII and EcoRI sites of pRAS117. (SEQ. ID NO. 49, as depicted in the Key to Sequence Listing set forth hereinafter).

Figure 10:
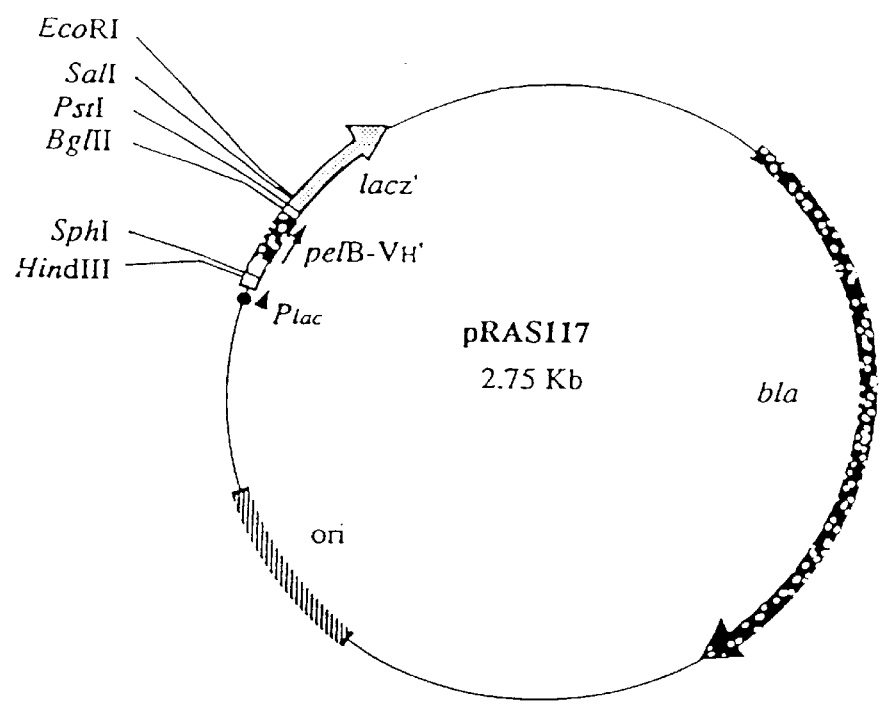

FIG. 10 shows a map of plasmid pRAS117.

Figure 11:
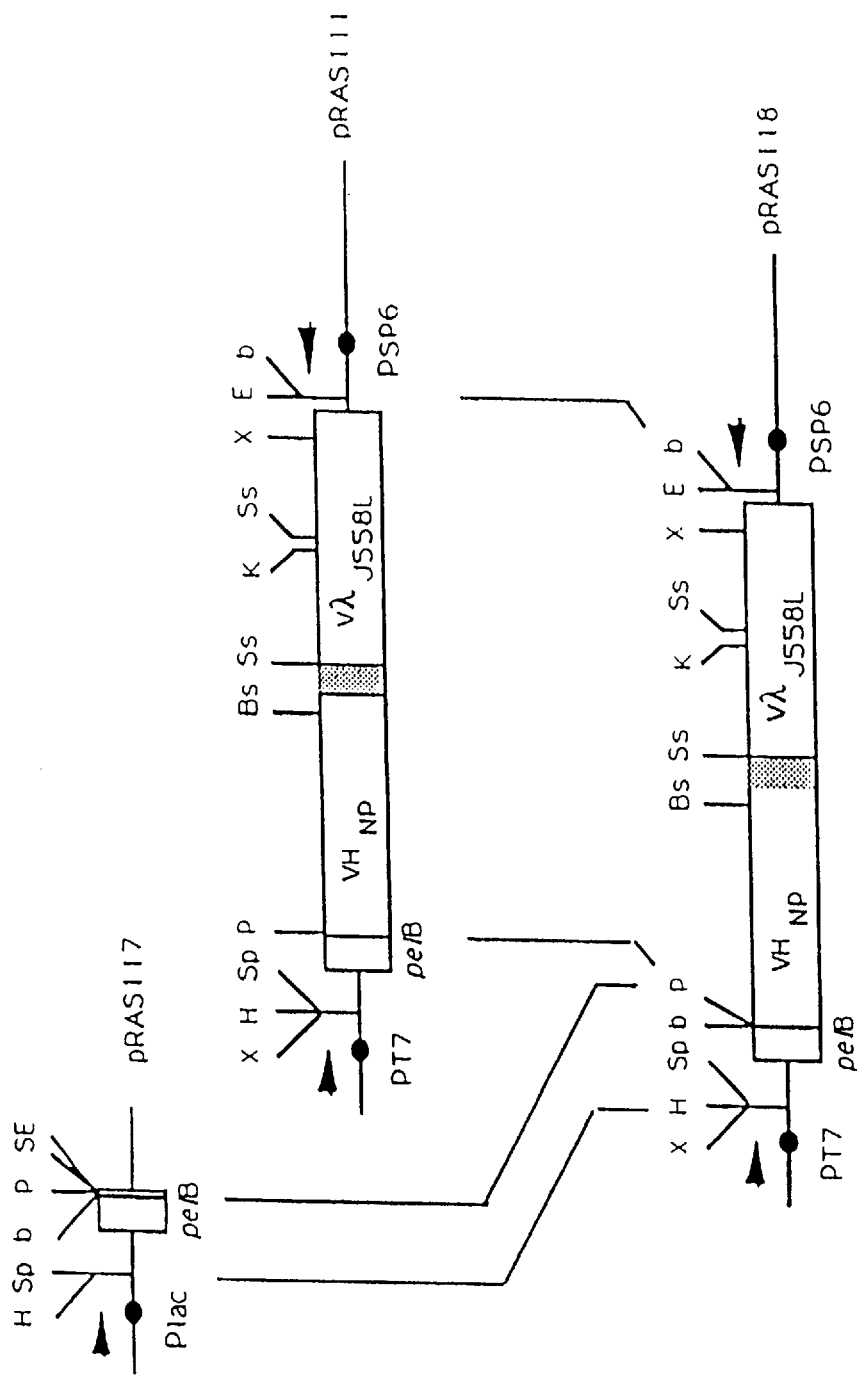

FIG. 11 is a diagrammatic representation of the construction of plasmid pRAS118.

FIG. 12 shows the sequences of oligonucleotides for amplifying Ad5 fibre DNA fragments. All oligonucleotides are presented 5'→3'. The reverse complements of FOR primers are shown. Derived amino acid sequences are shown where relevant. (SEQ. ID No. 51 through 69, as depicted in the Key to Sequence Listing set forth hereinafter).

FIG. 13 shows the nucleotide sequence and deduced amino acid sequence between the HindIII site and EcoRI site of pRAS111. (SEQ ID No. 71, as depicted in the Key to Sequence Listing set forth hereinafter).

Figure 14:
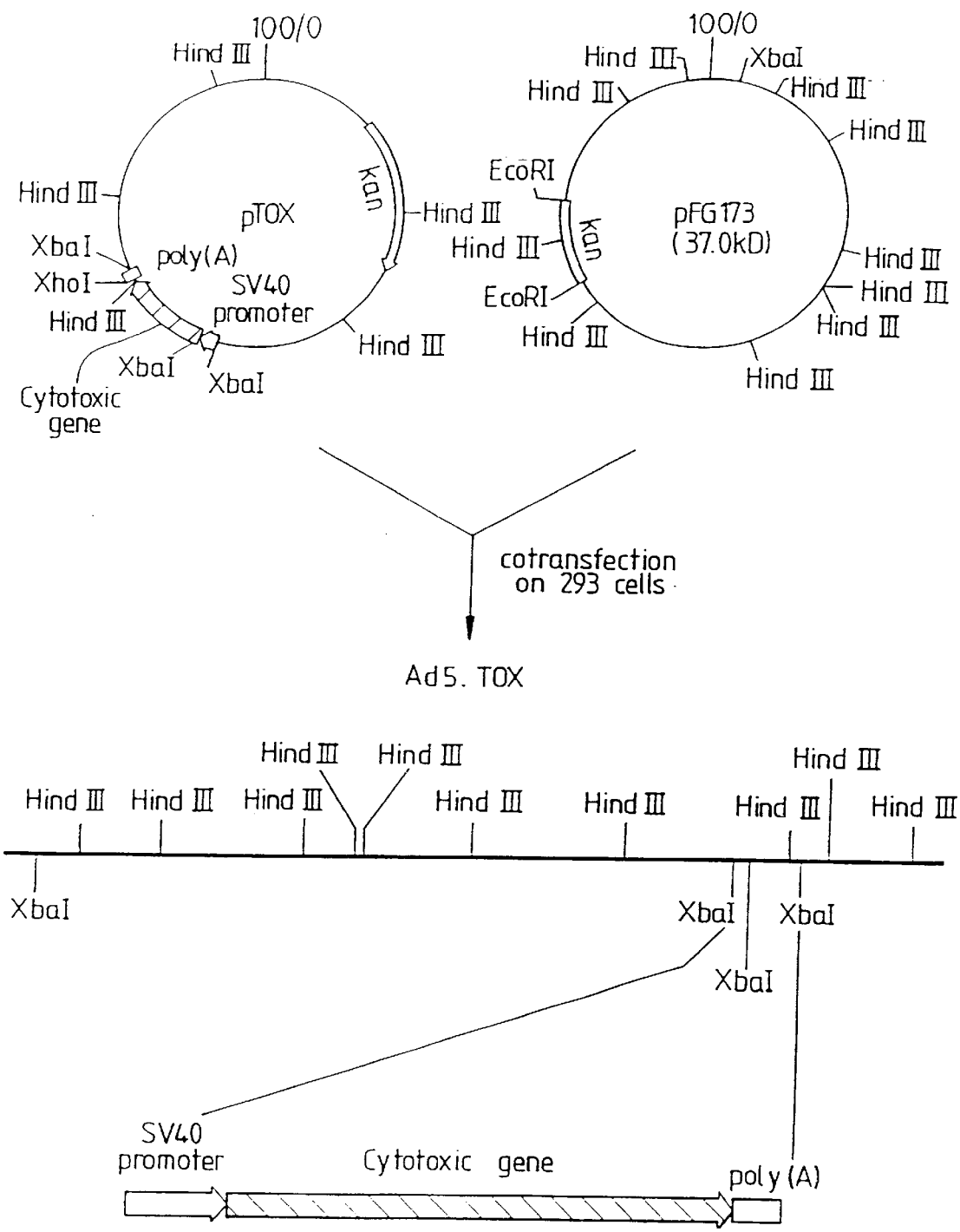

FIG. 14 gives a diagrammatic representation of constructing adenovirus carrying a cytotoxic gene.

FIG. 15(a) gives the nucleotide and amino acid sequences of mouse and humanised HMFG1 variable regions. (SEQ ID No. 73 as depicted in the Key to Sequence Listing set forth hereinafter).

FIG. 15(b) gives the nucleotide and amino acid sequences of mouse and humanised HMFG1 variable regions (SEQ ID No. 75).

EXAMPLE 1

Fusion sites within the adenovirus Ad5 fibre for binding moieties including single chain Fv (ScFv)

The Ad5 DNA sequence co-ordinates used here are taken from:

ADRCOMPGE_1: residues 1 to 32760 and

ADRCOMPGE_2: residues 32761–35935

These can be accessed by using program SEQ on the Intelligenetics database.

The sequence of Ad5 fibre can also be found in Chroboczek, J. and Jacrot, B. (1987) "The sequence of adenovirus fiber: Similarities and differences between serotypes 2 and 5" *Virology* 161, 549–554 and is available from the EMBL Database, Heidelberg, Germany under accession name ADEFIB.

Fusion sequences between the shaft and the ScFv are shown in FIG. 6. The fusion sites are at the junctions of the repetitive units of the shaft. Shaft sequences are shown in normal typescript; ScFv sequences are shown in italics. The DNA sequence between the PstI and XhoI sites is unique to the ScFv used.

Fusion A is at the end of the first repetitive unit of the shaft (co-ordinates 31218-9), fusion B at the end of the second (31266-7), fusion C at the third (31323-4), fusion D at the fourth (31368-9), fusion E at the fifth (31413-4), fusion F at the sixth (31458-9), fusion G at the seventh (31503-4), fusion H at the eighth (31551-2), fusion I at the ninth (31596-7), fusion J at the tenth (31641-2), fusion K at the eleventh (31692-3), fusion L at the twelfth (31737-8), fusion M at the thirteenth (31787-8), fusion N at the fourteenth (31836-7), fusion O at the fifteenth (31884-5), fusion P at the sixteenth (31929-30), fusion Q at the seventeenth (31995-6), fusion R at the eighteenth (32040-1), fusion S at the nineteenth (32103-4), fusion T at the twentieth (32151-2), fusion U at the twenty-first (32199-200), and fusion V is at the end of the twenty-second repetitive unit of the shaft (32244-5), the junction between shaft and knob.

EXAMPLE 2

Preparation of adenovirus expressing an ScFv on its surface

The genetically modified fibre is introduced into the Ad5 genome by: (a) replacing the fibre gene of plasmid pE4 with the modified fibre by standard recombinant DNA technology and (b) reconstituting the virus by recombination.

pE4 is a plasmid containing the right hand half of the Ad5 genome, and which has served as the source of the Ad5 fibre gene that we have used. It was provided by Dr Keith Leppard, Biological Sciences, University of Warwick, Coventry, CV4 7AL who has supplied details of its structure. If it is introduced into mammalian cells that contain the remainder of the Ad5 genome, then it is possible to obtain recombinants containing the modification. Most human cell lines can be used for the recombination but HeLa cells are preferred.

The plasmid pE4 is readily made in the following way. A derivative of pBR322 is made by digesting with BstN1 and rejoining using XhoI linkers such that the BstN1 fragment corresponding to positions 1442–2502 in the pBR322 sequence is removed. DNA from the adenovirus Ad5 strain 309 described by Jones & Shenk (1979) *Cell* 17, 683–689 is isolated and deproteinated. This DNA is then ligated to ClaI linkers and cut with EcoRI and ClaI. The ClaI-EcoRI fragment corresponding to the region of 76% of the Ad5 genome to the right hand end is isolated and cloned into the EcoRI-ClaI sites of the above-mentioned pBR322 derivative to form pE4.

Adenovirus Type 5 and HeLa cells are available from the American Type Culture Collection, 10801 University Blvd., Manassas, Va. 20110-2209, USA under accession numbers ATCC VR-5 and ATCC CCL-2.

Construction of plasmid pRAS117

Oligonucleotide primers LEADHBACK and LEADbFOR (FIG. 7) were used for PCR-mediated amplification of the DNA segment extending from the HindIII site of plasmid pRAS111, over the Shine-Dalgarno sequence and the pelB leader sequence to the PstI site in the ScFv. LEADbFOR directs the incorporation of a BglII site immediately after the pelB leader sequence. DNA (100 ng) from plasmid pRAS111 was subjected to 24 rounds of amplification, (94° C., 1 min; 65° C., 1.5 min and 72° C., 2 min) in a 50 $\mu$l reaction volume containing 25 pmol of each primer, 250 mM of each dNTP, 67 mM Tris-HCl (pH 8.8), 17 mM (NH$_4$)$_2$SO$_4$, 1.5 mM MgCl$_2$, 200 mg.ml$^{-1}$ gelatine and 5 units of *Thermus aquaticus* (Taq) polymerase (Cetus) overlaid with 25 $\mu$l paraffin oil. After the reaction, oil was removed by extraction with 500 $\mu$l chloroform. The sample was loaded on a 2% agarose gel, and the amplified fragment was electrophoresed on to a piece of NA45 paper (Schleicher and Schuell). Bound DNA was subsequently eluted by immersion in 400 $\mu$l 1M NaCl made in TE (10 mM Tris-HCl, pH 7.5, 1 mM EDTA) for 30 min at 70° C. To this was added 800 $\mu$l ethanol, and after incubation (2 h, -20° C.) the DNA was collected by centrifugation. The pellet was taken up in 50 $\mu$l T/E.

One fifth (10 $\mu$l) of the purified amplified fragment was cut with the restriction enzymes HindIII and PstI, in a total volume of 20 $\mu$l 50 mM Tris-HCl, pH 7.5, 10 MgCl2, 100 mM NaCl, 1 mM dithioerythreitol containing 10 units of each enzyme. After incubation (1 h, 37° C.) the reaction was stopped by incubation at 70° C. for 15 minutes.

The trimmed amplified fragment was cloned between the HindIII and PstI sites of pUC8, to generate plasmid pRAS117.

Plasmid pUC8 (1 $\mu$g) was cut with HindIII and PstI, in a total volume of 20 $\mu$l 50 mM Tris-HCl, pH 7.5, 10 MgCl$_2$, 100 mM NaCl, 1 mM dithioerythreitol containing 10 units of each enzyme. After incubation (1 h, 37° C.) the reaction was stopped by incubation at 70° C. for 15 minutes.

The ligation reaction contained 1.5 $\mu$l of pUC8/HindIII, PstI and 3 $\mu$l of the amplified leader/HindIII, PstI in a total volume of 15 $\mu$l containing 70 mM Tris-HCl pH 7.5, 7 mM MgCl$_2$, 0.7 mM rATP, 4 mM dithiothreitol, 0.5 mg.ml$^{-1}$ BSA and 10 units of T4 DNA ligase. After incubation (2 h, at room temperature), the reaction was stopped by the addition of 1 μl 500 mM EDTA, pH 8.0 and 14 μl H$_2$O.

This ligation mix was used to transform *E. coli.*

An aliquot (5 μl) of this ligation mix was used to transform a 200 μl aliquot of commercially available competent *E. coli* K12 DH58,1αF (Life Sciences Inc). After incubation (30 min, 0° C.), heat shock (2 min, 42° C.), addition of 800 μl L-broth and recovery (37° C., 1 h), cells (100 μl) were spread on L-agar plates containing 100 μg.ml$^{-1}$ ampicillin containing 50 mM IPTG (isopropyl-β-D-galactopyranoside) and 100 μg.ml$^{-1}$ X-Gal (5-bromo-4-chloro-3-indolyl-β-D-galactopyranoside). Cells were grown overnight at 37° C., and individual colonies were transferred to fresh L-agar/ampicillin plates. After 6 h growth, colonies were used to inoculate 5 ml aliquots of L-broth containing 100 μg.ml$^{31\ 1}$ ampicillin. These cells were grown overnight with shaking at 37° C., and used as a source of plasmid DNA.

These cells were used as a source of plasmid DNA.

Harvested cells were suspended in 360 μl of SET (50 mM sucrose, 10 mM EDTA, 100 mM Tris-HCl, pH 7.5) containing 2 mg.ml$^{-1}$ hen egg. lysozyme, transferred to a 1.5 ml microfuge tube, and diluted by addition of 300 μl 10% Triton X-100. After floating on boiling water for 2 min and cooling for a further minute in ice/water, denatured cell debris was removed by centrifugation (14,000×g, 20 min) in a microcentrifuge. The majority of the soluble remaining proteins were removed by addition of 300 μl 7.5M ammonium acetate and centrifugation (14,000×g, 10 min). Nucleic acids were precipitated by addition of 720 μl cold (-20° C.) isopropanol and centrifugation (14,000×g, 10 min). After rinsing the pellets with ethanol and drying, DNA was solubilised in 60 μl TE containing 170 μg.ml$^{-1}$ RNase A.

Restriction enzyme digestions on 5 μl aliquots, using the enzymes HindIII and BglII identified which of these plasmids were pRAS117. The construction scheme is shown in FIG. 8. The nucleotide and derived amino acid sequences between the HindIII and EcoRI sites of pRAS117 are shown in FIG. 9. A map of plasmid pRAS117 is provided in FIG. 10.

The nucleotide sequence of the relevant portion of pRAS111, between the HindIII site and EcoRI, site is given in FIG. 13.

Construction of plasmid pRAS118 (FIG. 11)

The 130 bp HindIII-PstI fragment of pRAS117 was used to replace the corresponding fragment of pRAS111, to generate plasmid pRAS118. An aliquot (2 μg) of pRAS111 DNA was cut with HindIII and PstI in the conditions used previously, the large fragment was isolated by electrophoresis onto NA45 paper, as described previously, and the DNA was suspended in 10 μl of TE. An aliquot (10 μl) of pRAS117 DNA was cut with HindIII and PstI in the conditions used previously, and the small fragment was isolated by electrophoresis onto NA45 paper, as described previously, and the DNA was suspended in 10 μl of TE.

The isolated pRAS111/HindIIIPstI large fragment (1.5 μl) and the isolated pRAS117HindIIIPstI small fragment (3 μl) were mixed and ligated in the conditions previously described.

Transformations, colony handling and DNA preparations were as previously described.

Restriction enzyme digestions on 5 μl aliquots, using the enzymes HindIII, PstI and BglII identified which of these plasmids were pRAS118. This encodes a NIP-reactive ScFv with a BglII cloning site immediately downstream of the pelb leader, suitable for inserting fragments of DNA from Ad5 fibre (and also suitable for fusion of any other desired fusion functions).

Amplification of Ad5 fibre DNA fragments

Fragments of DNA from Ad5 fibre were amplified by PCR using oligonucleotide TAILbBACK and oligonucleotide FIBREPFOR, FIBRE3FOR, FIBRE6FOR, FIBRE9FOR, FIBRE12FOR, FIBRE15FOR, FIBRE18FOR, FIBRE21FOR or FIBRE22FOR. Oligonucleotide sequences can be found in FIG. 12.

TAILdBACK directs the incorporation of a BglII site at the base of the fibre, and the FIBREnFOR series primers direct the incorporation of a PstI site at the junctions of repetitive shaft units 3–4 (FIBRE3FOR), 6–7 (FIBRE6FOR), 9–10 (FIBRE9FOR), 12–13 (FIBRE12FOR), 15–16 (FIBRE15FOR), 18–19 (FIBRE18FOR), 21–22 (FIBRE21FOR), between unit 22 and the knob (FIBRE22FOR) or at the end of the knob sequence (FIBREPFOR).

Fusion of fibre and ScFv

The amplified segments of fibre are trimmed with BglII and PstI and ligated between the BglII and PstI sites of plasmid pRAS118. This gives a range of fusions under the transcriptional control of the T7 promoter. Colonies are recovered after transformation of a suitable *E. coli* strain, such as DH5, which does not permit expression of the fusions.

Screening

Colonies containing candidates for fusion are identified by restriction digestion of their plasmid DNAs. These candidate DNAs are used to transform a suitable *E. coli* strain, such as BL21 (DE3), that contains a chromosomal insertion of T7 polymerase under lac control. In these cells, induction of expression of T7 polymerase using the gratuitous inducer IPTG causes expression of the fusion proteins. Soluble NIP-reactive material is identified in colonies with correctly assembled fusions. The DNA of these is identified and the NIP-reactive ScFv derived from pRAS111 are replaced with a cell-binding ScFv.

Replacing the fibre:ScFv in plasmid pE4

There is a HindIII site approximately half-way along the fibre gene. Fusions with long fibres also contain this HindIII site. The fusion is introduced at this site.

Recombination in vivo of plasmid pE4-ScFv with the adenovirus genome

To obtain virus particles expressing the ScFv on the penton fibre suitable cells, such as 293 cells, are cotransfected with plasmid pE4-ScFv and plasmid pFG173 as described in Mittal et al (1993) *Vines Res.* 28, 67–90, incorporated herein by reference. Since neither pFG173 nor pE4-ScFv individually is able to generate virus progeny, on transfection of 293 cells viable virus progeny are only produced by in vivo recombination between these two plasmids resulting in rescue of the penton fibre-ScFv fusion into the Ad5 genome.

293 cells are human transformed primary embryonal cells available from the ATCC under accession number ATCC CRL 1573.

The adenovirus particles made in this way express a NIP-binding ScFv on their surface. Such particles are useful in a two-step targeting approach wherein a target-cell specific binding moiety, such as those identified in Tables 1 and 2, are joined to NIP molecule and targeted to a cell. Once they have localized to the target cell within the patient, the adenovirus displaying NIP-binding ScFv is administered to the patient and binds to the NIP.

EXAMPLE 3

Insertion of a cytotoxic gene into the E3 region of adenovirus Ad5

In preparation for rescue of the cytotoxic gene into the E3 region of Ad5, the cytotoxic coding sequences were first inserted into a cassette containing the SV40 early promoter and poly A addition sequences to give plasmid pTOX as shown in FIG. 14.

To obtain virus with the cytotoxic gene and SV40 regulatory sequences in the E3 region, 293 cells are cotransfected with plasmids pTOX and pFG173 (FIG. 14). The plasmid pFG173 is constructed from pFG140, an infectious plasmid containing the Ad5 d1309 genome in circular form by inserting a kan$^r$ gene at the EcoRI site as 75.9 m.u. as described in Grahm (1984) *EMBO J.* 3, 2917–2922 and Mitall et al (1993) *Virus Res.* 28, 67–90.

Since neither pFG173 nor pTOX individually is able to generate infectious virus progeny, on transfection of 293 cells viable virus progeny are only produced by in vivo recombination between these two plasmids resulting in rescue of the E3 insert into the Ad5 genome.

Viral plaques obtained after cotransfection are isolated and expanded in 293 cells and viral DNA was analyzed on an agarose gel after digestion with HindIII. The structure of the desired Ad5-cytotoxic gene recombinant is verified by the presence of diagnostic fragments. One recombinant is plaque purified and used for further study.

Legend to FIG. 14

The plasmid pFG173 contains the entire Ad5 genome, except for a 3.2 kb sequence spontaneously deleted between m.u. 75.9–84.9. Plasmids pTOX and pFG173 were used for cotransfection of 293 cells to rescue, by in vivo recombination, the cytotoxic gene flanked by SV40 regulatory sequences in the E3 region of Ad5. The resulting Ad5-cytotoxic gene recombinant was named Ad5-TOX. The relative positions of HindIII and XbaI restriction sites of the Ad5-TOX genome are shown. The position and orientation of the SV40 promoter, the cytotoxic gene, and the SV40 polyadenylation signal are shown below. Solid bars: luciferase gene; open bars: SV40 promoter and SV40 polyadenylation signal; hatched bars: amp$^r$ and kan$^r$ genes.

The cytotoxic gene is the cDNA for thymidine kinase.

Other cytotoxic genes are inserted into the E3 region of Ad5 in an analogous manner.

EXAMPLE 4

Single chain Fv from the mouse monoclonal antibody HMFG1 and humanised monoclonal antibody Hu HMFG1

The nucleotide sequences encoding the $V_H$ heavy chains and $V_K$ light chains of HMFG1 and Hu HMFG1 are shown in FIG. 15 and are given in Verhoeyen et al (1993) *Immunology* 78, 364–370, incorporated herein by reference.

Legend to FIG. 15

Nucleotide and amino acid sequences of mouse and reshaped HMFG1 variable regions. (a) Heavy chain variable region sequences for mouse and reshaped HMFG1 (Mo $V_H$-HMFG1 and Hu $V_H$-HMFG1); (b) mouse and reshaped light chain variable regions respectively (Mo $V_k$-HMFG1 and Hu $V_k$-HMFG1). Amino acids numbering and definition of the CDR and framework regions are from Kabat et al (1987) *Sequences of Proteins of Immunological Interest*, Edn 4, US Dept of Health and Human Services Public Health Service, NIH, Bethesda, Md. 20892, USA.

The methods described by Bird et al (1988) *Science* 242, 423 or Huston et al (1988) *Proc. Natl. Acad. Sci. USA* 85, 5879 are applied to the nucleotide sequences described in FIG. 15 to generate genes encoding ScFv for HMFG1 and ScFv for Hu HMFG1. These genes are fused individually into the adenovirus penton fibre gene as described in Examples 1 and 2.

The amino acid sequences of the $V_H$ and $V_L$ chains of H17E2 are disclosed in "Monoclonal antibodies— applications in clinical oncology", pages 37–43, 1991, A. A. Epenetos, ed., Chapman & Hall, UK.

Nucleotide sequences encoding the $V_H$ and $V_L$ chains are readily derived from the amino acid sequence using the genetic code and an ScFv can be made from the sequences using the methods of Bird et al or Huston et al as described above.

| Key to Sequence Listing | | |
|---|---|---|
| | SEQ ID No. | |
| Name | Nucleotide Sequence | Polypeptide Sequence |
| Fusion A | 1 | 2 |
| Fusion B | 3 | 4 |
| Fusion C | 5 | 6 |
| Fusion D | 7 | 8 |
| Fusion E | 9 | 10 |
| Fusion F | 11 | 12 |
| Fusion G | 13 | 14 |
| Fusion H | 15 | 16 |
| Fusion I | 17 | 18 |
| Fusion J | 19 | 20 |
| Fusion K | 21 | 22 |
| Fusion L | 23 | 24 |
| Fusion M | 25 | 26 |
| Fusion N | 27 | 28 |
| Fusion O | 29 | 30 |
| Fusion P | 31 | 32 |
| Fusion Q | 33 | 34 |
| Fusion R | 35 | 36 |
| Fusion S | 37 | 38 |
| Fusion T | 39 | 40 |
| Fusion U | 41 | 42 |
| Fusion V | 43 | 44 |
| Xho-Eco | 45 | — |
| LEADHBACK | 46 | — |
| LEADbFOR | 47 | 48 |
| pRAS117 | 49 | 50 |
| TAILbBACK | 51 | 52 |
| FIBRE3FOR | 53 | 54 |
| FIBRE6FOR | 55 | 56 |
| FIBRE9FOR | 57 | 58 |
| FIBRE12FOR | 59 | 60 |
| FIBRE15FOR | 61 | 62 |
| FIBRE18FOR | 63 | 64 |
| FIBRE21FOR | 65 | 66 |
| FIBRE22FOR | 67 | 68 |
| FIBREPFOR | 69 | 70 |
| pRAS111 | 71 | 72 |
| MoV$_H$ | 73 | 74 |
| MoV$_k$ | 75 | 76 |
| HuV$_H$ | 77 | 78 |
| HuV$_k$ | 79 | 80 |

We claim:

1. An adenovirus, or adenovirus-like particle, haivng a penton fibre comprising a modified binding specificity conferred by a binding moiety which is heterologous to the adenovirus and is incorporated as a fusion protein with the fibre protein allowing the adenovirus or adenovirus-like particle to bind to a target cell which is not the natural host cell of the virus, characterized in that the said penton fibre is modified by the insertion or deletion or substitution of amino acid residues that disrupt the host-cell binding function so that the adenovirus or adenovirus-like particle is substantially incapable of binding the natural host cell.

2. An adenovirus or adenovirus-like particle according to claim 1 wherein the binding moiety is a monoclonal antibody, an ScFv, a dAb, or a minimal recognition unit of an antibody.

3. An adenovirus or adenovirus-like or virus-like particle according to claim 1 wherein the binding moiety is at least part of a ligand of a target cell-specific cell-surface receptor.

4. An adenovirus or adenovirus-like particle according, to claim 2 wherein the binding moiety recognizes a target cell specific surface antigen.

5. An adenovirus or adenovirus-like particle according to claim 3 wherein the target cell-specific cell-surface receptor is any one of GnRH receptor, MSH receptor and somatostatin receptor.

6. An adenovirus, or adenovirus-like particle, containing nucleic acid, according to claim 1 wherein the said adenovirus or adenovirus-like particle is adapted to deliver the said nucleic acid to the target cell.

7. An adenovirus or adenovirus-like particle according to claim 1 wherein the binding moiety is fused to the penton fibre protein at any one or more of the junctions of the repetitive units of the shaft.

8. An adenovirus or adenovirus-like particle according to claim 7 wherein the binding moiety is a ScFv.

9. An adenovirus or adenovirus-like particle according to claim 8 wherein the ScFv binds to a tumor cell antigen.

10. A nucleotide sequence encoding the penton fibre modified as defined in claim 1.

11. A nucleotide sequence defined in claim 10 additionally, comprising the remainder of the genome of the adenovirus or adenovirus-like particle.

12. A nucleotide sequence encoding an adenovirus or adenovirus-like particle according to claim 1.

13. A method for producing an adenovirus or adenovirus-like particle of claim 1 in cell culture, the method comprising (1) genetically modifying an adenovirus or adenovirus-like particle to produce a binding moiety which is incorporated as a fusion protein with the fibre protein, (2) infecting cells with the genetically modified adenovirus or adenovirus-like particle, (3) culturing the cells until the adenovirus or adenovirus-like particle reaches a sufficiently high titre and (4) harvesting and substantially purifying the genetically modified adenovirus or adenovirus-like particle.

14. An adenovirus or adenovirus-like particle having a penton fibre, comprising a modified binding specificity conferred by a binding moiety allowing the adenovirus or adenovirus-like particle to bind to a target cell, characterized in that the penton fibre protein is substantially incapable of binding the natural host cell and the binding moiety is fused to the penton fibre protein at any one or more of the junctions of the repetition units of the shaft.

* * * * *